United States Patent
Ayanoglu et al.

US009535074B2

(10) Patent No.: US 9,535,074 B2
(45) Date of Patent: Jan. 3, 2017

(54) IMMUNOASSAY FOR SOLUBLE PD-L1

(71) Applicant: Merck Sharp & Dohme Corp., Rahway, NJ (US)

(72) Inventors: Gulesi Ayanoglu, Palo Alto, CA (US); Xiaoyan Du, Jr., Burlingame, CA (US); Vinita Gupta, Edison, NJ (US); Omar Laterza, New York, NY (US); Linda Liang, Mountainview, CA (US); Eric Rimmer, Pacifica, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/843,285

(22) Filed: Sep. 2, 2015

(65) Prior Publication Data
US 2016/0069900 A1 Mar. 10, 2016

Related U.S. Application Data

(60) Provisional application No. 62/047,310, filed on Sep. 8, 2014.

(51) Int. Cl.
*G01N 33/68* (2006.01)
*G01N 33/574* (2006.01)

(52) U.S. Cl.
CPC .... *G01N 33/6872* (2013.01); *G01N 33/57426* (2013.01); *G01N 33/57488* (2013.01); *G01N 2333/70532* (2013.01); *G01N 2333/70596* (2013.01)

(58) Field of Classification Search
None
See application file for complete search history.

(56) References Cited

U.S. PATENT DOCUMENTS

| 7,521,051 B2 | 4/2009 | Collins et al. |
| 8,008,449 B2 | 8/2011 | Korman et al. |
| 8,354,509 B2 | 1/2013 | Carven et al. |
| 8,383,796 B2 | 2/2013 | Korman et al. |

FOREIGN PATENT DOCUMENTS

| WO | 2008156712 | 12/2008 |
| WO | 2010077634 | 7/2010 |
| WO | 2013019906 | 2/2013 |
| WO | 2014100079 | 6/2014 |
| WO | WO 2014165422 | * 10/2014 |

OTHER PUBLICATIONS

Ahmadzadeh et al., "Tumor antigen-specific CD8 T cells infiltrating the tumor express high levels of PD-1 and are functionally impaired", Blood, 2009, pp. 1537-1544, 114.

Chen, et al, "Development of a sandwich ELISA for evaluating soluble PD-L1 (CD274) in human sera of different ages as well as supernatants of PD-L1+ cell lines", Cytokine, 2011, pp. 231-238, vol. 56.

Dong et al., "Tumor-associated B7-H1 promotes T-cell apoptosis: A potential mechanism of immune evasion", Nature Medicine, 2002, pp. 793-800, 8(8).

Frigola et al., "Identification of a Soluble Form of B7-H1 That Retains Immunosuppressive Activity and Is Associated with Aggressive Renal Cell Carcinoma", Clin Cancer Res, 2011, pp. 1915-1923, 17(7).

Gadiot et al., "Overall Survival and PD-L1 Expression in Metastasized Malignant Melanoma", Cancer, 2011, pp. 2192-2201, 117.

Gao et al., "Overexpression of PD-L1 Significantly Associates with Tumor Aggressiveness and Postoperative Recurrence in Human Hepatocellular Carcinoma", Clinical Cancer Research, 2009, pp. 971-979, 15.

Ghebeh et al., "FOXP3+ Tregs and B7-H1+/PD-1+T lymphocytes co-infiltrate the tumor tissues of high-risk breast cancer patients: Implication for immunotherapy", BMC Cancer, 2008, pp. 57-68, 8.

Ghebeh et al., "The B7-H1 (PD-L1) T Lymphocyte-Inhibitory Molecule Is Expressed in Breast Cancer Patients with Infiltrating Ductal Carcinoma: Correlation with Important High-Risk Prognostic Factors", Neoplasia, 2006, pp. 190-198, 8.

Hamanishi et al., "Programmed cell death 1 ligand 1 and tumor-infiltrating CD8+ T lymphocytes are prognostic factors of human ovarian cancer", Proceedings of the National Academy of Sciences USA, 2007, pp. 3360-3365, 104.

Hamid et al., "Safety and Tumor Responses with Lambrolizumab (Anti-PD-1) in Melanoma", New Eng. J. Med., 2013, pp. 134-144, 369(2).

Hino et al., "Tumor cell expression of programmed cell death-1 ligand 1 is a prognostic factor for malignant melanoma", Cancer, 2010, pp. 1757-1766, 116(7).

Inman et al., "PD-L1 (B7-H1) expression by urothelial carcinoma of the bladder and BCG-induced granulomata: associations with localized stage progression", Cancer, 2007, pp. 1499-1505, 109.

Nakanishi et al., "Overexpression of B7-H1 (PD-L1) significantly associates with tumor grade and postoperative prognosis in human urothetial cancers", Cancer Immunol. Immunother, 2007, pp. 1173-1182, 56.

Nomi et al., "Clinical Significance and Therapeutic Potential of the Programmed Death-1 Ligand/Programmed Death-1 Pathway in Human Pancreatic Cancer", Clinical Cancer Research, 2007, pp. 2151-2157, 13.

Ohigashi et al., "Clinical Significance of Programmed Death-1 Ligand-1 and Programmed Death-1 Ligand-2 Expression in Human Esophageal Cancer", Clin. Cancer Research, 2005, pp. 2947-2953, 11.

Sharpe et al., "The function of programmed cell death 1 and its ligands in regulating autoimmunity and infection", Nature Immunology, 2007, pp. 239-245, 8.

Shimauchi et al., "Augmented expression of programmed death-1 in both neoplastic and non-neoplastic CD4+ T-cells in adult T-cell leukemia/lymphoma", Int. J. Cancer, 2007, pp. 2585-2590, 121.

(Continued)

*Primary Examiner* — Jacob Cheu
(74) *Attorney, Agent, or Firm* — Alysia A. Finnegan; Gloria M. Fuentes

(57) ABSTRACT

The present disclosure describes two matched antibody pairs for use in a sandwich immunoassay for detecting and quantifying soluble PD-L1 in liquid samples, as well as an electrochemiluminescence sandwich immunoassay that has been optimized and validated with one of the matched pairs.

17 Claims, 16 Drawing Sheets

(56) References Cited

OTHER PUBLICATIONS

Spigel et al., "Clinical activity, safety, and biomarkers of MPDL3280A, an engineered PD-L1 antibody in patients with locally advanced or metastatic non-small cell lung cancer (NSCLC)", J. Clin. Oncol., 2013, Abstract 8008, Suppl 31.

Taube et al., "Colocalization of Inflammatory Response with B7-H1 Expression in Inflammatory Response with B7-H1 Expression in Human Melanocytic Lesions Supports an Adaptive Resistance Mechanism of Immune Escape", Sci. Transl. Med., 2012, vol. 4, Issue 127, pp. 1-10.

Thompson et al., "Costimulatory B7-H1 in renal cell carcinoma patients: Indicator of tumor aggressiveness and potential therapeutic target", Proc. Nat'l Acad. Sci. USA, 2004, pp. 17174-17179, 101(49).

Thompson et al., "PD-1 Is Expressed by Tumor-Infiltrating Immune Cells and Is Associated with Poor Outcome for Patients with Renal Cell Carcinoma", Clinical Cancer Research, 2007, pp. 1757-1761, 15.

Thompson et al., "Tumor B7-H1 Is Associated with Poor Prognosis in Renal Cell Carcinoma Patients with Long-Term Follow-up", Cancer Res., 2006, pp. 3381-3385, 66.

Topalian et al., "Safety, Activity, and Immune Correlates of Anti-PD-1 Antibody in Cancer", New Eng. J. Med., 2012, pp. 2443-2454, 366(26).

WHO Drug Information, vol. 27, No. 1, pp. 68-69 (2013).

WHO Drug Information, vol. 27, No. 2, pp. 161-162 (2013).

Yang et al., "PD-L1: PD-1 Interaction Contributes to the Functional Suppression of T-Cell Responses to Human Uveal Melanoma Cells In Vitro", Invest Ophthalmol Vis Sci, 2008, pp. 2518-2525, 49(6).

* cited by examiner

Antibody 22C3

Light Chain Variable Region

[ATGGATTCACAGGCCCAGGTTCTTATATTGCTGCTGCTATGGGTATCTGGTACCTGTGGG]
GACATTGTGATGTCACAGTCTCCCTCCTCCCTGGCTGTGTCAGCAGGAGAGAAGGTCACTAT
GACCTGCAAATCCAGTCAGAGTCTGCTCCACACTAGCACCCGAAAGAACTACTTGGCTTGGT
ACCAGCAGAAACCAGGGCAGTCTCCTAAACTGCTGATCTATTGGGCATCCACTAGGGAATCT
GGGGTCCCTGATCGCTTCACAGGCAGTGGATCTGGGACAGATTTCACTCTCACCATCAGCAG
TGTGCAGGCTGAAGACCTGGCAGTTTATTACTGCAAACAATCTTATGATGTGGTCACGTTCG
GTGCTGGGACCAAGCTGGAGCTGAAA

[M D S Q A Q V L I L L L W V S G T C G]
D I V M S Q S P S S L A V S A G E K V T M T C K̲ S̲ S̲ Q̲ S̲ L̲ L̲ H̲
T̲ S̲ T̲ R̲ K̲ N̲ Y̲ L̲ A̲ W Y Q Q K P G Q S P K L L I Y W̲ A̲ S̲ T̲ R̲ E̲ S̲
G V P D R F T G S G S G T D F T L T I S S V Q A E D L A V Y Y
C K̲ Q̲ S̲ Y̲ D̲ V̲ V̲ T̲ F G A G T K L E L K

Heavy Chain Variable Region

[ATGGAAAGGCACTGGATCTTTCTCTTCCTGTTTTCAGTAACTGCAGGTGTCCACTCC]
CAGGTCCACCTTCAGCAGTCTGGGGCTGAACTGGCAAAACCTGGGGCCTCAGTGAAGATGTC
CTGCAAGGCTTCTGGCTACACGTTTACTAGTTACTGGATACACTGGATAAAGCAGAGGCCTG
GACAGGGTCTGGAATGGATTGGATACATTAATCCTTCCTCTGGTTATCATGAATACAATCAG
AAATTCATTGACAAGGCCACATTGACTGCTGACAGATCCTCCAGCACAGCCTACATGCACCT
GACCAGCCTGACGTCTGAAGACTCTGCAGTCTATTACTGTGCAAGATCGGGATGGTTAATAC
ATGGAGACTACTACTTTGACTTCTGGGGCCAAGGCACCACTCTCACAGTCTCCTCA

Antibody 5F9

Light Chain Variable Region

[ATGGAGTCACAGATTCAGGCATTTGTATTCGTGCTTCTCTGGTTGTCTGGTGTTGACGGA]
GACATTGTTATGACCCAGTCTCACAAATTCATGTCCACATCAGTAGGAGACAGGGTCAGCAT
CACCTGCAAGGCCAGTCAGGATACTAGTACTGCTGTAGCCTGGTATCAACAAAAACCAGGGC
AATCTCCTAAACTACTGATTTACTGGGCATCCACCCGGCACACTGGAGTCCCTGATCGCTTC
ACAGGCAGTGCATCTGGAATAGATTTTACTCTCACCATCAGCAGTTTGCAGGCTGAAGACCT
GGCACTTTATTATTGTCAGCAACATTATAGAACTCCGTGGACGTTCGGTGGAGGCACCAAGC
TGGAGATCAAA

[M E S Q I Q A F V F V L L W L S G V D G]
D I V M T Q S H K F M S T S V G D R V S I T C <u>K A S Q D T S T A V A</u> W Y Q Q K P
G Q S P K L L I Y <u>W A S T R H T</u> G V P D R F T G S A S G I D F T L T I S S L Q A
E D L A L Y Y C <u>Q Q H Y R T P W T</u> F G G G T K L E I K

Heavy Chain Variable Region

[ATGGGATGGAGCTGGATCTTTCTCTTCCTCTTGTCAGGAACTGCAGGCGTCCACTCT]
GAGGTCCACCTTCAGCAGTCAGGACCTGAACTGGTGAAACCTGGGGCCTCAGTGAAGATATC
CTGCAAGGCTTCTGGTGCCCCATTCACTGACTTCAACATCCACTGGATGAAACAGAGCCATG
GCGGGAGCCTTGAGTGGATTGGATCTATTTATCCTTACAATGGAAATACTAACTACAACCAG
AAGTTCAAGAACAAGGCCACATTGACTGTGGACGATTCCTCCATCACAGCCTACATGGAGTT
CCGCAGCCTGACATCTGAGGACTCTGCATTCTATTACTGTGCAAGAGGCTATATTGTTACGA
CTGCCTGGTTTGCTTATTGGGGCCAAGGGACTCTGGTCACTGTCTCTGCA

Antibody 13D2

Light Chain Variable Region

[ATGGATTTTCATGTGCAGATTTTCAGCTTCATGCTAATCAGTGTCACAGTCATATTGTCCA
GTGGA]
GAAATTGTGCTCACCCAGTCTCCAGCACTCATGGCTGCATCTCCAGGGGAGAAGGTCACCAT
CACCTGCAGTGTCAGCTCAAGTATAAGTTCCAGCAACTTGCACTGGTACCAGCAGAAGTCAG
AAACCTCCCCCAAACCCTGGATTTATGGCACATCCAACCTGGCTTCTGGAGTCCCTGTTCGC
TTCAGTGGCAGTGGATCTGGGACCTCTTATTCTCTCACAATCAGCAGCATGGAGGCTGAGGA
TGCTGCCACTTATTACTGTCAACAGTGGAGTAGTTACCCACTCACGTTCGGCTCGGGGACAA
AGTTGGAAATAAAA

[M D F H V Q I F S F M L I S V T V I L S S G]
E I V L T Q S P A L M A A S P G E K V T I T C <u>S V S S S I S S S N L H</u> W Y Q Q K
S E T S P K P W I Y <u>G T S N L A S</u> G V P V R F S G S G S G T S Y S L T I S S M E
A E D A A T Y Y C <u>Q Q W S S Y P L T</u> F G S G T K L E I K

Heavy Chain Variable Region

[ATGGAATGGAGATGGATCTTTCTCTTCCTCCTGTCAGGAACTACAGGTGTCCACTCT]
GAGATCCAGCTGCAGCAGTCTGGACCTGAGCTGGTGAAGCCTGGGGCTTCAGTGAAGGTATC
CTGCAAGGCTTCTGGTTATGCATTCACTAGCTACAAGATGTACTGGGTGAAGCAGAGCCATG
GAAAGAGCCTTGAGTGGATTGGATATATTGATCCTTACAATGGTGGTATTAACTACAACCAG
ATGTTCAAGGGCAAGGCCACATTGACTGTTGACAAGTCCTCCAGCACAGCCTACATGCATCT
CAACAGCCTGACATCTGAGGACTCTGCAGTCTATTACTGTGCAAGAGCCAAACAAGACATGC
CCCCTCCCTGGTTTGTTTACTGGGGCCAAGGGACTCTGGTCACTGTCTCTGCA

Immunohistochemical detection of PD-L1 on human melanoma cell lines with 22C3

NFD: non fasted day
FD: fasted day
M: male
F: Female

IMMUNOASSAY FOR SOLUBLE PD-L1

FIELD OF THE INVENTION

The present invention relates generally to biomarkers expressed by cancer cells. In particular, the invention relates to the identification and assay of biomarkers useful for studying the role of the Programmed Death 1 (PD-1) signaling pathway in cancer progression and treatment.

BACKGROUND OF THE INVENTION

PD-1 is recognized as an important player in immune regulation and the maintenance of peripheral tolerance. PD-1 is moderately expressed on naive T, B and NKT cells and up-regulated by T/B cell receptor signaling on lymphocytes, monocytes and myeloid cells (1). Two known ligands for PD-1, PD-L1 (B7-H1) and PD-L2 (B7-DC), are expressed in human cancers arising in various tissues, and PD-L1 expression has been associated with poor prognosis and reduced overall survival, irrespective of subsequent treatment, in studies on different cancers, e.g., ovarian, renal, colorectal, pancreatic, liver cancers and melanoma (2-12). Similarly, PD-1 expression on tumor infiltrating lymphocytes was found to mark dysfunctional T cells in breast cancer and melanoma (13-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies (mAbs) that inhibit the interaction between PD-1 and one or both of its ligands PD-L1 and PD-L2 are in clinical development for treating cancer. These include nivolumab and pembrolizumab, which bind to PD-1, and MPDL3280A, which binds to PD-L1 (17-19). While clinical studies with these PD-1 antagonists have produced durable anti-tumor responses in some cancer types, a significant number of patients failed to exhibit an anti-tumor response.

Tumor expression of PD-L1 has been investigated as a predictive biomarker to identify tumors that are likely to respond to anti-PD-1 blockade, and published studies have generally described immunohistochemistry (IHC) analysis of frozen or formalin-fixed, paraffin-embedded (FFPE) tumor tissue sections stained with a primary antibody that binds to membrane-bound PD-L1 (20-23).

Recently, an enzyme-linked immunosorbent assay (ELISA) was used to detect a soluble form of PD-L1 (sPD-L1) in human serum and in the culture supernatant of PD-L1 expressing cells (24). Because sPD-L1 levels in cell culture supernatants were lower in the presence of a matrix metalloproteinase inhibitor (MMPI), and correlated with the expression of membrane-bound PD-L1 (mPD-L1) on the cells, it was proposed that sPD-L1 is produced through proteolytic cleavage of mPD-L1. Also, since sPD-L1 has been shown to bind to PD-1, have immunosuppressive activity and is associated with aggressive renal cell carcinoma, it has been proposed that circulating sPD-L1 can contribute to tumor immune evasion (25). Thus, a need exists for sensitive and specific assays to detect sPD-L1 in human serum.

SUMMARY OF THE INVENTION

The inventors herein have identified two matched pairs of binding molecules that bind to the extracellular domain of PD-L1 and provide similar sensitivity and specificity when used as capture and detector binding molecules in a sandwich immunoassay for detecting sPD-L1 in a liquid sample. The capture binding molecule in each of these sPD-L1 binding pairs comprises the six CDR sequences of antibody 22C3.138, which is described in WO2014/100079 and comprises the mature light chain and heavy chain amino acid sequences shown in FIG. 1 (SEQ ID NOs: 1 and 2, respectively). In one PD-L1 binding pair, the detector binding molecule comprises the six CDR sequences of antibody 5F9, which comprises the mature light chain and heavy chain amino acid sequences shown in FIG. 2 (SEQ ID NOs: 3 and 4, respectively). The detector binding molecule in the other PD-L1 binding pair comprises the six CDR sequences of antibody 13D2, which comprises the mature light chain and heavy chain amino acid sequences shown in FIG. 3 (SEQ ID NOs: 5 and 6, respectively).

The inventors have also developed an electrochemiluminescent (ECL) sandwich immunoassay for detecting and quantifying human sPD-L1 in a serum or plasma sample that employs either of these PD-L1 binding pairs and buffers optimized to prevent the potential for interference by endogenous compounds (e.g., PD-L2) and therapeutic agents (e.g., an anti-PD-1 mAb). This ECL assay may be useful to quantify sPD-L1 in serum samples and tissue culture supernatants to study the role of sPD-L1 in immunoregulatory pathways and in the prognosis of patients with cancer.

Thus, in one aspect, the present invention provides a kit for detecting soluble human Programmed Cell Death 1 Ligand 1 (shPD-L1) in a liquid sample. The kit comprises the capture binding molecule described above, one of the detector binding molecule described above and optionally one or more reagents that are used with the binding molecules to perform a sandwich immunoassay. In an embodiment, the capture binding molecule is immobilized on a solid support and the detector binding molecule comprises a detectable label. In some embodiments, the immunoassay is an electrochemiluminescent assay and the detectable label is capable of emitting light upon exposure to a microvoltage. In an embodiment, the kit comprises a solid support that is coated with streptavidin, the capture binding molecule is biotinylated and the detector binding molecule is labeled with an amine reactive, N-hydroxysuccinimide ester that has the structure shown in FIG. 4.

The capture binding molecule is an isolated antibody or antigen binding fragment thereof that specifically binds shPD-L1 and comprises three light chain CDRs of SEQ ID NOs: 7, 8 and 9 and three heavy chain CDRs of SEQ ID NOs: 13, 14 and 15. In some embodiments, the capture binding molecule comprises a light chain variable region of SEQ ID NO:1 and a heavy chain variable region of SEQ ID NO:2.

The detector binding molecule is an isolated antibody or antigen binding fragment thereof that is capable of specifically binding to shPD-L1 molecules that are complexed with antibody 22C3 molecules and which comprises: (a) three light chain CDRs of SEQ ID NOs: 19, 20 and 21 and three heavy chain CDRs of SEQ ID NOs: 25, 26 and 27; or (b) three light chain CDRs of SEQ ID NOs: 31, 32 and 33 and three heavy chain CDRs of SEQ ID NOs: 37, 38 and 39. In some embodiments, the detector binding molecule comprises: (a) a light chain variable region of SEQ ID NO:3 and a heavy chain variable region of SEQ ID NO:4; or (b) a light chain variable region of SEQ ID NO:5 and a heavy chain variable region of SEQ ID NO:6.

In another aspect, the invention provides an assay for detecting shPD-L1 in a liquid sample that employs one of the paired capture and detection binding molecules described above. The immunoassay comprises providing a solid substrate that is coated with the capture binding molecule, incubating the sample with the solid substrate under conditions suitable for formation of a first complex between the capture binding molecule and shPD-L1 in the sample, washing the solid substrate at least once with a wash buffer, incubating the detector binding molecule with the solid substrate under conditions suitable for formation of a second complex between the captured shPD-L1 and the detection binding molecule, washing the solid substrate at least once with the wash buffer, and detecting the second complex. In some embodiments, the capture binding molecule is bound directly to the solid substrate. In other embodiments, the capture binding molecule is bound to a substance immobilized on the solid substrate. In some embodiments, the capture binding molecule is biotinylated and the immobilized substance is avidin. In some embodiments, the solid substrate is a 96 well microtiter plate coated with streptavidin.

The second complex may be detected directly or indirectly. In direct embodiments, the detector binding molecule comprises a detectable label, while in indirect embodiments, the detector binding molecule is not labeled and the second complex is detected by incubating the substrate with a detectably labeled antibody that is specific for the detector binding molecule.

In some embodiments, the liquid sample comprises serum or plasma prepared from a blood sample removed from a subject with a cancer and in some preferred embodiments, the cancer is non-small-cell lung cancer (NSCLC) or multiple myeloma.

BRIEF DESCRIPTION OF THE DRAWINGS

FIG. 1 shows the nucleotide sequences for the variable light and heavy chain cDNA (SEQ ID NOs: 12 and 18) prepared from total RNA isolated from the hybridoma that expresses antibody 20C3 and the predicted amino acid sequences encoded thereby (bold font, SEQ ID NOs: 11 and 17), with brackets indicating nucleotide and amino acid sequences for the leader peptide and underlining indicating the CDR amino acid sequences.

FIG. 2 shows the nucleotide sequences for the variable light and heavy chain cDNA (SEQ ID NOs: 24 and 30) prepared from total RNA isolated from the hybridoma expressing antibody 5F9 and the predicted amino acid sequences encoded thereby (bold font, SEQ ID NOs: 23 and 29), with brackets indicating nucleotide and amino acid sequences for the leader peptide and underlining indicating the CDR amino acid sequences.

FIG. 3 shows the nucleotide sequences for the variable light and heavy chain cDNA (SEQ ID NOs: 36 and 42) prepared from total RNA isolated from the hybridoma expressing antibody 13D2 and the predicted amino acid sequences encoded thereby (bold font, SEQ ID NOs: 35 and 41), with brackets indicating nucleotide and amino acid sequences for the leader peptide and underlining indicating the CDR amino acid sequences.

DETAILED DESCRIPTION

Figure 4:
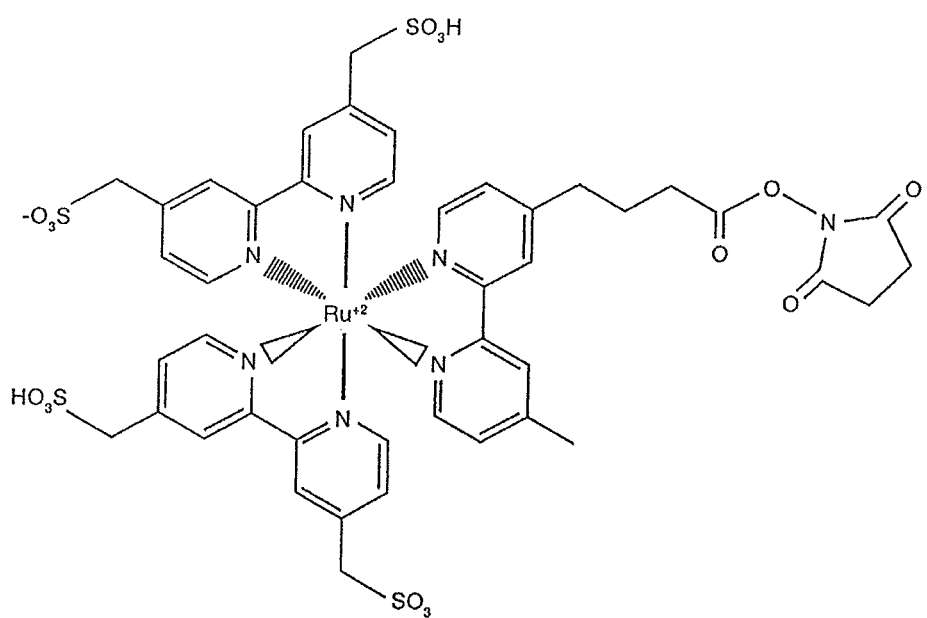
FIG. 4 shows the structure of ruthenium tris-bipyridine chelate, which is commercially available as MSD® SULFO-TAG NHS-Ester from Meso Scale Discovery® (Gaithersburg, Md.).

Abbreviations. Throughout the detailed description and examples of the invention the following abbreviations will be used:
CDR Complementarity determining region
CHO Chinese hamster ovary
CR Complete Response
DFS Disease free survival
FFPE formalin-fixed, paraffin-embedded
FR Framework region
HRP Horseradish peroxidase
IgG Immunoglobulin G
IHC Immunohistochemistry or immunohistochemical
MSD Meso Scale Discovery
OR Overall response
OS Overall survival
PD Progressive Disease
PD-1 Programmed Death 1
PD-L1 Programmed Cell Death 1 Ligand 1
PD-L2 Programmed Cell Death 1 Ligand 2
PFS Progression free survival (PFS)
PR Partial Response
RECIST Response Evaluation Criteria in Solid Tumors
SD Stable Disease
VH Immunoglobulin heavy chain variable region
VK Immunoglobulin kappa light chain variable region I. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the gene signature score for a gene signature discussed herein, or the dosage of a PD-1 antagonist, or the length of treatment time with a PD-1 antagonist) means that the parameter may vary by as much as 10% above or below the stated numerical value for that parameter. For example, a proximity threshold score of about 0.2% includes scores of 0.18%, 0.19%, 0.20%, 0.21% and 0.22%.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized or fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In some embodiments, reference to an antibody herein refers to a tetramer structural unit. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md. ; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or antigen binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be treated in accordance with the present invention include those characterized by elevated expression of one or both of PD-L1 and PD-L2 in tested tissue samples.

"CDR" or "CDRs" as used herein means complementarity determining region(s) in an immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Clothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |

TABLE 1-continued

Exemplary Conservative Amino Acid Substitutions

| Original residue | Conservative substitution |
| --- | --- |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

"Framework region" or "FR" as used herein means the immunoglobulin variable regions excluding the CDR regions.

"Isolated" as applied to a biological molecule such as an antibody, nucleic acid, peptide, polypeptide or protein refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"Patient" or "subject" refers to any single human subject for which therapy is desired or that is participating in a clinical trial, epidemiological study or used as a control,.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful as PD-1 antagonists in the various aspects and embodiments of the present invention, are described in U.S. Pat. No. 7,521,051, U.S. Pat. No. 8,008,449, and U.S. Pat. No. 8,354,509. Specific anti-human PD-1 mAbs useful as the PD-1 antagonist in the various aspects and embodiments of the present invention include: MK-3475, a humanized IgG4 mAb with the structure described in *WHO Drug Information*, Vol. 27, No. 2, pages 161-162 (2013); nivolumab (BMS-936558), a human IgG4 mAb with the structure described in *WHO Drug Information*, Vol. 27, No. 1, pages 68-69 (2013) and the humanized antibodies h409A11, h409A16 and h409A17, which are described in WO2008/156712.

Examples of mAbs that bind to human PD-L1, and useful as PD-1 antagonists in any of the various aspects and embodiments of the present invention, are described in WO2013/019906, WO2010/077634 A1 and U.S. Pat. No. 8,383,796. Specific anti-human PD-L1 mAbs useful as the PD-1 antagonist in the various aspects and embodiments of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, compositions and uses of the present invention include AMP-224 (also known as B7-DCIg), which is a PD-L2-FC fusion protein and binds to human PD-1.

"Sample" when referring to a tumor or any other biological material referenced herein, means a sample that has been removed from the subject; thus, none of the testing methods described herein are performed in or on the patient.

Soluble human PD-L1, shPD-L1 and sPD-L1 each refer to a polypeptide comprising the N-terminal segment of the extracellular domain of human B7-H1 ((amino acids 19-239) NP_054862.1) or a portion thereof that is bound by an antibody comprising a light chain variable region of SEQ ID NO:1 and a heavy chain variable region of SEQ ID NO:2. A sPD-L1 polypeptide may naturally occur in a subject or be recombinantly produced. A recombinantly produced sPD-L1 may comprise a C-terminal polyhistidine tag (HIS-TAG sPD-L1) and is useful as a standard control in performing immunoassays of the invention.

"Treat" or "treating" a cancer as used herein means to administer a PD-1 antagonist of other therapeutic agent to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, J. Nucl. Med. 50:1S-10S (2009); Eisenhauer et al., supra). In some preferred embodiments, response to a PD-1 antagonist is assessed using RECIST 1.1 criteria. In some embodiments, the treatment achieved by a therapeutically effective amount is any of PR, CR, PFS, DFS, OR or OS. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Variable regions" or "V region" as used herein means the segment of IgG chains which is variable in sequence between different antibodies. It extends to Kabat residue 109 in the light chain and 113 in the heavy chain.

II. Capture Binding Molecule

The capture binding molecule is an antibody which comprises the six CDRs of the antibody 22C3, or an antigen binding fragment of said antibody. Table 2 below lists the sequences for various features in antibody 22C3.

in the framework region (i.e., outside of the CDRs). Similarly, a variant heavy chain variable region sequence is identical to the reference sequence except having one, two, three, four, five, six, seven, eight, nine or ten conservative amino acid substitutions in the framework region (i.e., outside of the CDRs).

TABLE 2

Monoclonal Antibody 22C3

| Antibody Feature | Sequence | SEQ ID NO |
|---|---|---|
| *Light Chain* | | |
| CDRL1 | KSSQSLLHTSTRKNYLA | 7 |
| CDRL2 | WASTRES | 8 |
| CDRL3 | KQSYDVVT | 9 |
| Leader Sequence | MDSQAQVLILLLLWVSGTCG | 10 |
| Variable Region | MDSQAQVLILLLLWVSGTCGDIVMSQSPSSLAVSAGEKVTMTCKSSQ SLLHTSTRKNYLAWYQQKPGQSPKLLIYWASTRESGVPDRFTGSGSG TDFTLTISSVQAEDLAVYYCKQSYDVVTFGAGTKLELK | 11 |
| Mature Variable Region | DIVMSQSPSSLAVSAGEKVTMTCKSSQSLLHTSTRKNYLAWYQQKPG QSPKLLIYWASTRESGVPDRFTGSGSGTDFTLTISSVQAEDLAVYYC KQSYDVVTFGAGTKLELK | 1 |
| DNA Sequence Encoding Variable Region | ATGGATTCACAGGCCCAGGTTCTTATATTGCTGCTGCTATGGGTATC TGGTACCTGTGGGGACATTGTGATGTCACAGTCTCCCTCCTCCCTGG CTGTGTCAGCAGGAGAGAAGGTCACTATGACCTGCAAATCCAGTCAG AGTCTGCTCCACACTAGCACCCGAAAGAACTACTTGGCTTGGTACCA GCAGAAACCAGGGCAGTCTCCTAAACTGCTGATCTATTGGGCATCCA CTAGGGAATCTGGGGTCCCTGATCGCTTCACAGGCAGTGGATCTGGG ACAGATTTCACTCTCACCATCAGCAGTGTGCAGGCTGAAGACCTGGC AGTTTATTACTGCAAACAATCTTATGATGTGGTCACGTTCGGTGCTG GGACCAAGCTGGAGCTGAAA | 12 |
| *Heavy Chain* | | |
| CDRH1 Kabat Def'n | SYWIH | 13 |
| CDRH2 | YINPSSGYHEYNQKFID | 14 |
| CDRH3 | SGWLIHGDYYFDF | 15 |
| Leader Sequence | MERHWIFLFLFSVTAGVHS | 16 |
| Variable Region | MERHWIFLFLFSVTAGVHSQVHLQQSGAELAKPGASVKMSCKASGYT FTSYWIHWIKQRPGQGLEWIGYINPSSGYHEYNQKFIDKATLTADRS SSTAYMHLTSLTSEDSAVYYCARSGWLIHGDYYFDFWGQGTTLTVSS | 17 |
| Mature Variable Region | QVHLQQSGAELAKPGASVKMSCKASGYTFTSYWIHWIKQRPGQGLEW IGYINPSSGYHEYNQKFIDKATLTADRSSSTAYMHLTSLTSEDSAVY YCARSGWLIHGDYYFDFWGQGTTLTVSS | 2 |
| DNA Sequence Encoding Variable Region | ATGGAAAGGCACTGGATCTTTCTCTTCCTGTTTTCAGTAACTGCAGG TGTCCACTCCCAGGTCCACCTTCAGCAGTCTGGGGCTGAACTGGCAA AACCTGGGGCCTCAGTGAAGATGTCCTGCAAGGCTTCTGGCTACACG TTTACTAGTTACTGGATACACTGGATAAAGCAGAGGCCTGGACAGGG TCTGGAATGGATTGGATACATTAATCCTTCCTCTGGTTATCATGAAT ACAATCAGAAATTCATTGACAAGGCCACATTGACTGCTGACAGATCC TCCAGCACAGCCTACATGCACCTGACCAGCCTGACGTCTGAAGACTC TGCAGTCTATTACTGTGCAAGATCGGGATGGTTAATACATGGAGACT ACTACTTTGACTTCTGGGGCCAAGGCACCACTCTCACAGTCTCCTCA | 18 |

In an embodiment, the capture binding molecule comprises a light chain variable region of SEQ ID NO:1 or a variant of SEQ ID NO:1 and a heavy chain variable region of SEQ ID NO:2 or a variant or SEQ ID NO:2. In such embodiments, a variant light chain variable region sequence is identical to the reference sequence except having one, two, three, four or five conservative amino acid substitutions To facilitate its use in immunoassays, the capture binding molecule may also comprise a moiety that allows the capture binding molecule to bind to a solid surface, either directly by covalent bonding or indirectly by affinity binding. Commonly used cross-linking agents for attaching the capture binding molecule to the solid phase substrate include, e.g., 1,1-bis(diazoacetyl)-2-phenylethane, glutaraldehyde, N-hydroxy-succinimide esters, for example, esters with 4-azido-salicylic acid, homobifunctional imidoesters, including disuccinimidyl esters such as 3,3'-dithiobis-(succinimidylpropionate), and bifunctional maleimides such as bis-N-maleimido-1,8-octane. Examples of affinity binding pairs that can be used for coating the solid surface with the capture binding molecule include, e.g.: biotin/avidin; biotin/streptavidin; biotin/anti-biotin; avidin/anti-avidin; thyroxine/thyroxine-binding globulin; carbohydrate/lectins; hapten/anti-hapten antibody; vitamin B12/intrinsic factor; and cortisol/cortisol binding protein. In an embodiment, the capture binding molecule is a biotinylated monoclonal antibody and comprises a light chain variable region of SEQ ID NO:1 and a heavy chain variable region of SEQ ID NO 2.

III. Detector Binding Molecule

The detector binding molecule is an antibody, or antigen binding fragment thereof, which comprises the six CDRs of the antibody 5F9 or the six CDRs of the antibody 13D2. Tables 3 and 4 below list the sequences for various features in antibody 5F9 and antibody 13D2, respectively.

TABLE 3

Monoclonal Antibody 5F9

| Antibody Feature | Sequence | SEQ ID NO |
|---|---|---|
| Light Chain | | |
| CDRL1 | KASQDTSTAVA | 19 |
| CDRL2 | WASTRHT | 20 |
| CDRL3 | QQHYRTPWT | 21 |
| Leader Sequence | MESQIQAFVFVLLWLSGVDG | 22 |
| Variable Region | MESQIQAFVFVLLWLSGVDGDIVMTQSHKFMSTSVGDRVSITCKASQDTSTAVAWYQQKPGQSPKLLIYWASTRHTGVPDRFTGSASGIDFTLTISSLQAEDLALYYCQQHYRTPWTFGGGTKLEIK | 23 |
| Mature Variable Region | DIVMTQSHKFMSTSVGDRVSITCKASQDTSTAVAWYQQKPGQSPKLLIYWASTRHTGVPDRFTGSASGIDFTLTISSLQAEDLALYYCQQHYRTPWTFGGGTKLEIK | 3 |
| DNA Sequence Encoding Variable Region | ATGGAGTCACAGATTCAGGCATTTGTATTCGTGCTTCTCTGGTTGTCTGGTGTTGACGGAGACATTGTTATGACCCAGTCTCACAAATTCATGTCCACATCAGTAGGAGACAGGGTCAGCATCACCTGCAAGGCCAGTCAGGATACTAGTACTGCTGTAGCCTGGTATCAACAAAAACCAGGGCAATCTCCTAAACTACTGATTTACTGGGCATCCACCCGGCACACTGGAGTCCCTGATCGCTTCACAGGCAGTGCATCTGGAATAGATTTTACTCTCACCATCAGCAGTTTGCAGGCTGAAGACCTGGCACTTTATTATTGTCAGCAACATTATAGAACTCCGTGGACGTTCGGTGGAGGCACCAAGCTGGAGATCAAA | 24 |
| Heavy Chain | | |
| CDRH1 Kabat Def'n | DFNIH | 25 |
| CDRH2 | SIYPYNGNTNYNQKFKN | 26 |
| CDRH3 | GYIVTTAWFAY | 27 |
| Leader Sequence | MGWSWIFLFLLSGTAGVHS | 28 |
| Variable Region | MGWSWIFLFLLSGTAGVHSEVHLQQSGPELVKPGASVKISCKASGAPFTDFNIHWMKQSHGGSLEWIGSIYPYNGNTNYNQKFKNKATLTVDDSSITAYMEFRSLTSEDSAFYYCARGYIVTTAWFAYWGQGTLVTVSA | 29 |
| Mature Variable Region | EVHLQQSGPELVKPGASVKISCKASGAPFTDFNIHWMKQSHGGSLEWIGSIYPYNGNTNYNQKFKNKATLTVDDSSITAYMEFRSLTSEDSAFYYCARGYIVTTAWFAYWGQGTLVTVSA | 4 |
| DNA Sequence Encoding Variable Region | ATGGGATGGAGCTGGATCTTTCTCTTCCTCTTGTCAGGAACTGCAGGCGTCCACTCTGAGGTCCACCTTCAGCAGTCAGGACCTGAACTGGTGAAACCTGGGGCCTCAGTGAAGATATCCTGCAAGGCTTCTGGTGCCCCATTCACTGACTTCAACATCCACTGGATGAAACAGAGCCATGGCGGGAGCCTTGAGTGGATTGGATCTATTTATCCTTACAATGGAAATACTAACTACAACCAGAAGTTCAAGAACAAGGCCACATTGACTGTGGACGATTCCTCCATCACAGCCTACATGGAGTTCCGCAGCCTGACATCTGAGGACTCTGCATTCTATTACTGTGCAAGAGGCTATATTGTTACGACTGCCTGGTTTGCTTATTGGGGCCAAGGGACTCTGGTCACTGTCTCTGCA | 30 |

TABLE 4

Monoclonal Antibody 13D2

| Antibody Feature | Sequence | SEQ ID NO |
|---|---|---|
| Light Chain | | |
| CDRL1 | SVSSSISSSNLH | 31 |
| CDRL2 | GTSNLAS | 32 |
| CDRL3 | QQWSSYPLT | 33 |
| Leader Sequence | MDFHVQIFSFMLISVTVILSSG | 34 |
| Variable Region | MDFHVQIFSFMLISVTVILSSGEIVLTQSPALMAASPGEKVTITCSVSSSISSSNLHWYQQKSETSPKPWIYGTSNLASGVPVRFSGSGSGTSYSLTISSMEAEDAATYYCQQWSSYPLTFGSGTKLEIK | 35 |
| Mature Variable Region | EIVLTQSPALMAASPGEKVTITCSVSSSISSSNLHWYQQKSETSPKPWIYGTSNLASGVPVRFSGSGSGTSYSLTISSMEAEDAATYYCQQWSSYPLTFGSGTKLEIK | 5 |
| DNA Sequence Encoding Variable Region | ATGGATTTTCATGTGCAGATTTTCAGCTTCATGCTAATCAGTGTCACAGTCATATTGTCCAGTGGAGAAATTGTGCTCACCCAGTCTCCAGCACTCATGGCTGCATCTCCAGGGGAGAAGGTCACCATCACCTGCAGTGTCAGCTCAAGTATAAGTTCCAGCAACTTGCACTGGTACCAGCAGAAGTCAGAAACCTCCCCCAAACCCTGGATTTATGGCACATCCAACCTGGCTTCTGGAGTCCCTGTTCGCTTCAGTGGCAGTGGATCTGGGACCTCTTATTCTCTCACAATCAGCAGCATGGAGGCTGAGGATGCTGCCACTTATTACTGTCAACAGTGGAGTAGTTACCCACTCACGTTCGGCTCGGGGACAAAGTTGGAAATAAAA | 36 |
| Heavy Chain | | |
| CDRH1 Kabat Def'n | SYKMY | 37 |
| CDRH2 | YIDPYNGGINYNQMFK | 38 |
| CDRH3 | AKQDMPPPWFVY | 39 |
| Leader Sequence | MEWRWIFLFLLSGTTGVHS | 40 |
| Variable Region | MEWRWIFLFLLSGTTGVHSEIQLQQSGPELVKPGASVKVSCKASGYAFTSYKMYWVKQSHGKSLEWIGYIDPYNGGINYNQMFKGKATLTVDKSSSTAYMHLNSLTSEDSAVYYCARAKQDMPPPWFVYWGQGTLVTVSA | 41 |
| Mature Variable Region | EIQLQQSGPELVKPGASVKVSCKASGYAFTSYKMYWVKQSHGKSLEWIGYIDPYNGGINYNQMFKGKATLTVDKSSSTAYMHLNSLTSEDSAVYYCARAKQDMPPPWFVYWGQGTLVTVSA | 6 |
| DNA Sequence Encoding Variable Region | ATGGAATGGAGATGGATCTTTCTCTTCCTCCTGTCAGGAACTACAGGTGTCCACTCTGAGATCCAGCTGCAGCAGTCTGGACCTGAGCTGGTGAAGCCTGGGGCTTCAGTGAAGGTATCCTGCAAGGCTTCTGGTTATGCATTCACTAGCTACAAGATGTACTGGGTGAAGCAGAGCCATGGAAAGAGCCTTGAGTGGATTGGATATATTGATCCTTACAATGGTGGTATTAACTACAACCAGATGTTCAAGGGCAAGGCCACATTGACTGTTGACAAGTCCTCCAGCACAGCCTACATGCATCTCAACAGCCTGACATCTGAGGACTCTGCAGTCTATTACTGTGCAAGAGCCAAACAAGACATGCCCCCTCCCTGGTTTGTTTACTGGGGCCAAGGGACTCTGGTCACTGTCTCTGCA | 42 |

In an embodiment, the detector binding molecule is an antibody which comprises a light chain variable region of SEQ ID NO:3 or a variant of SEQ ID NO:3 and a heavy chain variable region of SEQ ID NO:4 or a variant or SEQ ID NO:4. In another embodiment, the detector binding molecule comprises a light chain variable region of SEQ ID NO:5 or a variant of SEQ ID NO:5 and a heavy chain variable region of SEQ ID NO:6 or a variant or SEQ ID NO:6. In either embodiment, a variant light chain variable region sequence is identical to the reference sequence except having one, two, three, four or five conservative amino acid substitutions in the framework region (i.e., outside of the CDRs). Similarly, a variant heavy chain variable region sequence is identical to the reference sequence except having one, two, three, four, five, six, seven, eight, nine or ten conservative amino acid substitutions in the framework region (i.e., outside of the CDRs).

To facilitate its use in immunoassays, the detector binding molecule may also comprise a detectable label. The detectable label may be any moiety that does not interfere with the binding of the detector binding molecule to complexes formed between the capture binding molecule and sPD-L1. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting. Other radionuclides include $^{99}Tc$, $^{90}Y$, $^{111}In$, $^{32}P$, $^{11}C$, $^{15}O$, $^{13}N$, $^{18}F$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}P$, $^{234}Th$, and $^{40}K$, $^{157}Gd$, $^{55}Mn$, $^{52}Tr$, and $^{56}Fe$.

(b) Colloidal gold particles.

(c) Fluorescent or chemiluminescent labels including, but not limited to, rare earth chelates (europium chelates), fluorescein and its derivatives, rhodamine and its derivatives, isothiocyanate, phycoerythrin, phycocyanin, allophycocyanin, o-phthaladehyde, fluorescamine, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, a ruthenylated amine reactive, N-hydroxysuccinimide ester label, Texas Red, dansyl, Lissamine, umbelliferone, phycocrytherin, phycocyanin, or commercially available fluorophores. The fluorescent labels can be conjugated to the antibody using the techniques disclosed in *Current Protocols in Immunology*, supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor.

Examples of enzymatic labels include luciferases (e.g. firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langbne & H. Van Vunakis), Academic press, New York, 73:147-166 (1981).

Examples of enzyme-substrate combinations are:

(i) Horseradish peroxidase (HRP) with hydrogen peroxidase as a substrate, wherein the hydrogen peroxidase oxidizes a dye precursor, such as, e.g., 3,3' diamino benzidine (DAB), which produces a brown end product; 3-amino-9-ethylcarbazole (AEC), which upon oxidation forms a rose-red end product; 4-chloro-1-napthol (CN), which precipitates as a blue end product; and p-Phenylenediamine dihydrochloride/pyrocatecol, which generates a blue-black product; orthophenylene diamine (OPD) and 3,3',5,5'-tetramethyl benzidine hydrochloride (TMB);

(ii) alkaline phosphatase (AP) and para-Nitrophenyl phosphate, naphthol AS-MX phosphate, Fast Red TR and Fast Blue BB, napthol AS-BI phosphate, napthol AS-TR phosphate, 5-bromo-4-chloro-3-indoxyl phosphate (BCIP), Fast Red LB, Fast Garnet GBC, Nitro Blue Tetrazolium (NBT), and iodonitrotetrazolium violet (INT); and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies are conventional and very well known in the art.

In some embodiments, the label is indirectly conjugated with the antibody. The skilled artisan will be aware of various techniques for achieving this. For example, the antibody can be conjugated with an affinity binding pair. If an affinity binding pair is utilized to immobilize the capture binding molecule to the solid substrate, then the affinity binding pair used to label the detector binding molecule should not be a different affinity binding pair.

In an embodiment, the detector binding molecule is a monoclonal antibody that is labeled with the compound that has the structure shown in FIG. 4 and comprises: (a) a light chain variable region of SEQ ID NO:3 and a heavy chain variable region of SEQ ID NO 4; or (b) a light chain variable region of SEQ ID NO:5 and a heavy chain variable region of SEQ ID NO 6.

IV. Immunoassays Kits

Kits of the invention comprise a capture binding molecule as described above, and a detector binding molecule as described above.

The kit may also comprise a solid substrate that is capable of being coated with the capture binding molecule, either by covalent or affinity binding interactions as described above. In such embodiments, the solid surface is preferably coated with avidin or streptavidin. Alternatively, the kit comprises the solid surface with the capture binding molecule immobilized to the surface.

The solid support used for immobilization of the capture binding molecule may be any inert support or carrier that is essentially water insoluble and useful in immunoassays, including supports in the form of, e.g., flat surfaces, particles, porous matrices, etc. Examples of commonly used supports include small sheets, beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195, 128; 4,247,642; 4,229,537; and 4,330,440 are suitably employed for immobilizing the capture binding molecule.

In one embodiment, the immobilized capture reagent is coated on a streptavidin-coated 96 well microtiter plate, such as, e.g., the MULTI-ARRAY® 96-well Strepatvidin Gold Plate sold under catalog number L15SA/L11SA by MESO SCALE DISCOVERY® (Rockville, Md.).

When the detector binding molecule is labeled, the kit may also comprise one or more reagents capable of producing a detectable signal when a sandwich is formed between the capture binding molecule, sPD-L1 analyte and the detector binding molecule. For enzyme-labeled detector binding molecules, the kit may include substrates and cofactors required by the enzyme, and for fluorophore labels, the kit may include a dye precursor that produces a detectable chromophore.

If the detector binding molecule is not labeled, the kit may also comprise a detection means, such as a labeled antibody that specifically binds to the detector binding molecule.

In an embodiment, the kit of the invention comprises a biotinylated capture binding molecule, a detector binding molecule labeled with a compound that has the structure in FIG. 4 and a streptavidin coated 96-well microtiter assay plate, wherein the biotinylated capture binding molecule is a monoclonal antibody which comprises a light chain variable region of SEQ ID NO:1 and a heavy chain variable region of SEQ ID NO 2 and the labeled detector binding molecule is a monoclonal antibody which comprises: (a) a light chain variable region of SEQ ID NO:3 and a heavy chain variable region of SEQ ID NO 4; or (b) a light chain variable region of SEQ ID NO:5 and a heavy chain variable region of SEQ ID NO 6.

V. Immunoassays

The matched capture and detector binding pairs described herein may be used in a variety of sandwich immunoassays to detect and/or quantitate human sPD-L1 in a sample removed from a patient. Such assays include, e.g., enzyme-linked immunoassay, radioimmunoassay, fluorescence immunoassay, and electrochemiluminescent (ECL) immunoassay. The sample may be any of a variety of body fluids, including blood, serum, semen, breast exudate, saliva, sputum, urine, cytosols, plasma, ascites, pleural effusions, amniotic fluid, bladder washes, bronchioalveolar lavages, and cerebrospinal fluid. In some embodiments, the sample consists essentially of blood, serum or plasma, and in one preferred embodiment, the sample consists essentially of serum. It is also contemplated that the matched capture and detector binding pairs described herein may be used to assay for sPD-L1 in a tumor tissue sample.

In some embodiments, liquid samples (e.g., serum, plasma, purified sPD-L1 solution) are assayed for sPD-L1 using a sandwich ECL immunoassay, which is performed in one or more 96-well streptavidin-coated microtiter plates, and employs biotinylated antibody 22C3 as the capture binding molecule and either the 5F9 antibody or 13D2 antibody labeled with ruthenium tris-bipyridine chelate (FIG. 4) as the detector binding molecule. Such ECL immunoassays may conveniently employ the Multi-Array® platform and STREPTAVIDIN GOLD microtiter plate marketed by Meso Scale Discovery® (MSD, Rockville, Md.) The MSD STREPTAVIDIN GOLD plate is a 96-well, single spot plate with a hydrophobic surface and streptavidin bound to an electrode surface in the bottom of each well, and has an IgG binding capacity of 0.3 pmole/well.

A sandwich ECL immunoassay using one of the matched antibody pairs described herein and the MSD Multi-Array® platform generally comprises: (a) contacting the plate with a first blocking solution and incubating the plate under conditions suitable to block non-specific binding sites for the biotinylated capture molecule; (b) washing the plate to remove the first blocking solution; (c) coating the plate with the biotinylated capture antibody; (d) washing the plate to remove unbound capture antibody; (e) contacting the plate with a second blocking solution; (f) adding to separate wells in the plate one or more test samples, at least three different known amounts of a purified, recombinantly produced sPD-L1 for use as positive controls and generating a standard curve, and one or more negative controls; (g) incubating the plate under conditions suitable for binding of sPD-L1 to the capture antibody to occur; (h) washing the plate to remove unbound sPD-L1; (i) contacting the plate with the labeled detector antibody and incubating the plate under conditions suitable for binding of the detector antibody to complexes between sPD-L1 and the capture antibody; and (j) washing the plate to remove unbound labeled detection antibody; (k) instructing a Meso Scale Discovery SECTOR™ Imager to apply a voltage to the bottom of the plate and read the resulting ECL signal initiated from electrochemical stimulation of the label on the detector antibody. The intensity of the ECL signal reflects the concentration of sPD-L1 in the sample and thus in one embodiment, the immunoassay method further comprises determining the concentration of sPD-L1 in at least one of the test samples by comparing the intensity of the ECL signal for the test sample to the ECL signals for the standard curve. Various embodiments for performing individual steps in this immunoassay are described below.

Step (a): Examples of appropriate blocking agents include, e.g., gelatin, bovine serum albumin, egg albumin, and casein. This first blocking step is conveniently performed at about 4° C. for 8 to 72 hours or at ambient temperature (e.g., about 25° C.) for about 1-4 hours. In a preferred embodiment, about 150 microliters of a blocking solution (5% BSA in phosphate buffered saline (PBS)) is added to each well of the microtitre plate, the plate is covered with a plate seal and shaken at 700 rpm on a plate shaker for about 12-18 hours at about 4° C. A Heidolph Titramax 101, LabLine Titer Plate Shaker or equivalent of either plate shaker is conveniently used for this and subsequent shaking steps in the immunoassay.

Step (b): The blocking solution is removed by adding to the wells a wash solution, which typically comprises a physiologic buffer such as Tris-buffered saline (TBS) or phosphate-buffered saline (PBS) at a pH range of 6-9 and may also comprise a detergent such as Tween-20. This washing step may be performed at a temperature from about 4° C. to about 25° C. and repeated two or more times. In a preferred embodiment, the wash step is performed three times and comprises adding about 200 microliters of a wash buffer (0.05% Tween 20 in PBS, pH 7.4, or an equivalent) to the plate wells at about 25° C. A BioTek ELx405 plate washer, or an equivalent, is conveniently used for this and subsequent washing steps.

Step (c): The blocked and washed pate is incubated with the biotinylated capture antibody under conditions that allow affinity binding to occur between biotin molecules on the capture antibody and streptavidin molecules on the plate. The amount of capture antibody added to each plate well should be less than the binding capacity of the plate well, and will generally depend on the expected concentration range of sPD-L1 in the sample(s) to be assayed. The skilled artisan may readily determine empirically an appropriate concentration of capture antibody to maximize the sensitivity of the assay over the concentration range of interest. In a preferred embodiment, 25 microliters of a solution of biotinylated capture antibody at 2 micrograms/ml is added to each well of the microtiter plate, the plate is covered with a plate seal and then shaken at 700 rpm on a plate shaker for one hour at ambient temperature (e.g., about 25° C.). A higher concentrated stock solution of capture antibody is conveniently diluted to the desired concentration using MSD Diluent 100 (MSD Cat. No. R50AA), which comprises a blend of stabilizers and blocking agent in phosphate buffered saline.

Step (d): Unbound capture antibody is then removed by washing the plate in a wash buffer. In a preferred embodiment, this wash step is performed three times and comprises adding about 200 microliters of a wash buffer (0.05% Tween 20 in PBS, pH 7.4, or an equivalent) to the plate wells at about 25° C.

Step (e): A second blocking step is performed to reduce binding to the capture antibody of heterophilic antibodies that may be present in the human plasma or serum sample. Typical blocking reagents for this purpose include non-specific immunoglobulin molecules such as mouse IgG, mouse serum, nonspecific monoclonal antibodies, aggregated IgG and the like. In an embodiment, the second blocking solution comprises at least one specific immuno-globulin binder that is directed against human heterophilic antibodies typically present in plasma and serum samples. Such a blocking reagent is marketed by Scantibodies Laboratory, Inc. (Santee Calif.) as HBR-1 (Cat. No. 3KC533). In a preferred embodiment, 25 microliters of the HBR-1 blocking reagent, which has been diluted with MSD Diluent 2 (Meso Scale Discovery, Cat. No. R51BB-2) to a final concentration of about 400 to about 2,400 micrograms/ml, is added to each plate well, and the plate is shaken briefly at 700 RPM to disperse the diluent and blocking reagent.

Step (f): In a preferred embodiment, 25 microliters of each test sample, sPD-L1 standard solution, and negative control desired to be used is added to the appropriate well on the assay plate, the plate is covered with a plate seal and then shaken at 700 rpm for two hours on a plate shaker at about 25° C.

Test Samples: Depending on the suspected level of sPD-L1 in a subject's serum or plasma sample, the sample may be used directly, or it may be desirable to use a two- to four-fold dilution of the sample in the immunoassay. In a preferred embodiment, the test sample is diluted four-fold in MSD Diluent 2 (Meso Discovery, Cat. No. R51BB-2). Serum samples are conveniently prepared by collecting whole blood into BD Vacutainer® Red Top Tubes (i.e., contains a clot activator) (BD Diagnostics, Franklin Lakes, N.J.), allowing the collected samples to clot at room temperature for about 30 minutes, centrifuging the tubes at about 1,700×g (3000 RPM) for 0 min at 4° C. The serum samples are typically stored at −70° C. or below until analyses.

sPD-L1 Standards: The sPD-L1 standard solution typically comprises a HIS-TAG PD-L1 polypeptide, which comprises amino acids 19-239 of NP_054862.1, and is conveniently obtained from Sino Biological (Beijing, P.R. China, Cat No. 10084-H08H). In a preferred embodiment, 25 microliters each of eight different standard control solutions comprising different concentrations of HIS-TAG PD-L1 are added to separate plate wells for use as standards for generating a standard curve:

Standard 1=2,400 picogram(pg)/ml;
Standard 2=800 pg/ml;
Standard 3=266.7 pg/ml;
Standard 4=88.9 pg/ml;
Standard 5=29.6 pg/ml;
Standard 6=9.9 pg/ml;
Standard 7=3.3 pg/ml; and
Standard 8=1.1 pg/ml.

The standard sPD-L1 solutions are prepared in a preferred embodiment by making serial dilutions starting from a 10× working stock solution comprising 24,000 pg/ml HIS-TAG PD-L1 (Sino Biologicals Cat No. 10084-H08H) in MSD Diluent 2 (Meso Scale Discovery, Cat No. R51BB-2). sPD-L1 standards with other concentration ranges may be used, such as e.g., seven serially diluted standard solutions that range from 4000 pg/ml HIS-TAG sPD-L1 to 5.5 pg/ml HIS-TAG sPD-L1.

Negative Control(s): More than one plate well may be configured as a negative control. In an embodiment, each negative control well is prepared by adding 25 microliters of the same diluent solution used for the test samples and standards, e.g., MSD Diluent 2 (Meso Scale Discovery, Cat No. R51BB-2).

Step (g): The plate containing the test samples, standards and control(s) added in step (f) is covered with a plate seal and incubated for two hours at about 25° C. while shaking on a plate shaker set for 700 rpm.

Step (h): Unbound sPD-L1 is removed by washing the plate in a wash buffer. In a preferred embodiment, this wash step is performed three times and comprises adding about 200 microliters of a wash buffer (0.05% Tween 20 in PBS, pH 7.4, or an equivalent) to the plate wells at about 25° C.

Step (i): In a preferred n embodiment, 25 microliters of a solution containing 1 microgram/ml of the labeled detection antibody is added to each plate well. This solution is conveniently prepared from a stock solution of labeled detection antibody during the incubation period in step (g) using MSD Diluent 100 (Meso Discovery, Cat. No. R50AA-2). After addition of the labeled detection antibody, the plate is covered with a plate sealer and opaque lid to protect the plate contents from light. In a preferred embodiment, the covered plate is incubated at about 25° C. for one hour while shaking a plate shaker set for 700 rpm.

Step (j): Unbound labeled detection antibody is removed by washing the plate in a wash buffer. In a preferred embodiment, this wash step is performed three times and comprises adding about 200 microliters of a wash buffer (0.05% Tween 20 in PBS, pH 7.4, or an equivalent) to the plate wells at about 25° C.

Step (k): In a preferred embodiment, the washed plate from step (j) is prepared for generation and reading of the ECL signal by adding 150 microliters of a 1× read buffer, which is a dilution from 4× Read Buffer T With Surfactant from Meso Scale Discovery (Cat. No. R92TC-2). The plate is then placed in the Meso Scale Discovery SECTOR™ Imager 6000 for generation and reading of the ECL signal. In a preferred embodiment, the assay results are analyzed using the DISCOVERY WORKBENCH® Software 3.0 from Meso Scale Discovery.

The preferred embodiment of the ECL sandwich immunoassay described above is capable of the following performance characteristics on human serum test samples when employed with the biotinylated antibody 22C3 as the capture binding molecule and the 5F9 antibody labeled with ruthenium tris-bipyridine chelate (FIG. 4) as the detector antibody: linearity of 80-120% [define over what dilution, concentration ranges], intra-assay precision for sPD-L1 concentration variance (CV) of ≤6%; inter-assay precision for sPD-L1 CV of ≤9%, and a lower limit of quantitation (LLOQ) of 4.4 pg/ml.

Soluble PD-L1 levels in a patient diagnosed with a tumor may be determined in samples removed from the patient before and/or after exposure of the patient to one or more therapeutic agents, e.g. a PD-1 antagonist or a chemotherapeutic agent or another biotherapeutic agent. Accordingly, samples of blood or other suitable bodily fluids may be removed from a patient over a period of time. The patient's tumor may be primary or recurrent, and may be of any type (as described above), any stage (e.g., Stage I, II, III, or IV or an equivalent of other staging system), and/or histology. The subject may be of any age, gender, treatment history and/or extent and duration of remission.

Each of the steps of obtaining a patient blood sample, performing the immunoassay, and analyzing the results may be performed by separate individuals at separate locations. In some embodiments, the individuals involved with preparing and assaying a patient sample for sPD-L1 do not know the identity of the patient whose sample is being tested; i.e., the sample received by a diagnostic laboratory is made anonymous in some manner before being sent to the laboratory. For example, the sample may be merely identified by a number or some other code (a "sample ID") and the results of the assay are reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report and provides the report to the patient's physician or to the patient. In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

EXAMPLES

Example 1

Identification of Matched Capture and Detector Antibody Pairs

The inventors undertook a screening process to identify matched capture and detector pairs of antibodies for use in a quantitative ECL immunoassay for sPD-L1. The inventors established several criteria for the matched antibody pairs and the immunoassay: (1) the capture and detector antibodies should recognize two different non-overlapping epitopes such that when the analyte of interest binds to the capture antibody, the epitope recognized by the detector antibody must not be obscured or altered; (2) lack of cross-reactivity or interference by PD-1, PD-L2, or a therapeutic anti-PD-1 mAb that may be present in the sample and (3) a minimum detectable concentration of <50 pg/ml sPD-L1 in an appropriately diluted serum or plasma sample.

Fifty-six potential capture/detection pairs were screened for reactivity with a HIS-TAG sPD-L1, a PD-L1:Fc fusion protein, a PD-L2:Fc fusion protein and endogenous PD-L1 (in human serum). These fifty-six pairs were based on nine monoclonal antibodies that bind to human PD-L1. Antibodies 1-7 were provided by Merck Research Laboratories (MRL, Palo Alto, Calif.) as separate biotinylated and sulfotagged versions, antibody 8 was biotinylated 29E.2A3, obtained from BioLegend (San Diego, Calif.) and antibody 9 was the biotinylated mouse monoclonal anti-CD274, IgG2b Kappa member of a commercially available matched ELISA pair manufactured by Abnova in Taiwan (Cat. No. H00029126-AP41.

In this initial screen 37/56 pairs failed to satisfy one or more of the required criteria. The remaining 19 capture: detector antibody pairs were subjected to a second round of screening using the same PD ligand agents employed in the first screen, and four of these pairs provided superior results by various criteria, including high ECL signal with a four-point HIS-TAG sPD-L1 standard curve, sensitivity (<10 pg/ml HIS-TAG sPD-L1) and strong reactivity with serum. These four pairs were screened for reactivity with HIS-TAG sPD-L1 in a wider range of test materials, including normal plasma, myeloma serum, transient transfection supernatant and HIS-TAG sPD-L1 spiked into plasma.

Two matched antibody pairs (22C3 as capture Ab and 5F9 or 13D2 as detector Ab) performed very similarly in this third screen, with the 22C3:5F9 pair having a lower limit of quantitation (LLOQ) of about 1 pg/ml (Pair 1) and the 22C3:13D2 pair (Pair 2) having a LLOQ of about 3 pg/ml. Tables 5A-5C below show the performance characteristics for Pair 1 and Pair 2 in terms of specificity, i.e., lack of cross-reactivity for and lack of interference by PD-1 and PD-L2.

TABLE 5A

Test for interference of matched antibody for cross-reactivity with PD-1 or PD-L2.

| Analyte | [pg/ml] | Pair 1 (Ab3/Ab5) | Pair 2 (Ab3/Ab6) |
|---|---|---|---|
| PD-1/Fc | 10000 | ND | ND |
|  | 1000 | ND | ND |
|  | 100 | ND | ND |
|  | 10 | ND | ND |
| PD-L2/Fc | 10000 | ND | ND |
|  | 1000 | ND | ND |
|  | 100 | ND | ND |
|  | 10 | ND | ND |

ND = not detected

TABLE 5B

Test for Interference with 10,000 pg/ml PD-1.

| | Pair 1 (Ab3/Ab5) | | Pair 2 (Ab3/Ab6) | |
|---|---|---|---|---|
| PD-L1 pg/ml | measured sPD-L1 | % recovery | measured sPD-L1 | % recovery |
| 250 | 239.0 | 95.6 | 237.7 | 95.1 |
| 62.5 | 60.5 | 96.8 | 66.6 | 106.6 |
| 15.6 | 15.8 | 101.3 | 15.8 | 101.3 |
| 3.9 | 3.6 | 92.3 | 4 | 102.6 |

TABLE 5C

Test for Interference with 10,000 pg/ml PD-L2.

| | Pair 1 (Ab3/Ab5) | | Pair 2 (Ab3/Ab6) | |
|---|---|---|---|---|
| PD-L1 pg/ml | measured sPD-L1 | % recovery | measured sPD-L1 | % recovery |
| 250 | 219.1 | 87.6 | 255.5 | 102.2 |
| 62.5 | 61.1 | 97.8 | 69.4 | 111.0 |
| 15.6 | 15.3 | 98.1 | 16.4 | 105.1 |
| 3.9 | 3.6 | 92.3 | 4.2 | 107.7 |

Example 2

Specificity of the 22C3:5F9 Pair for PD-L1

To confirm that ECL signal was generated by reactivity of each antibody in the matched pair with sPD-L1, three serum test samples were diluted ⅕ and absorbed against agarose beads coupled to capture Ab 22C3 (Ab3), detector Ab 5F9

Figure 5:
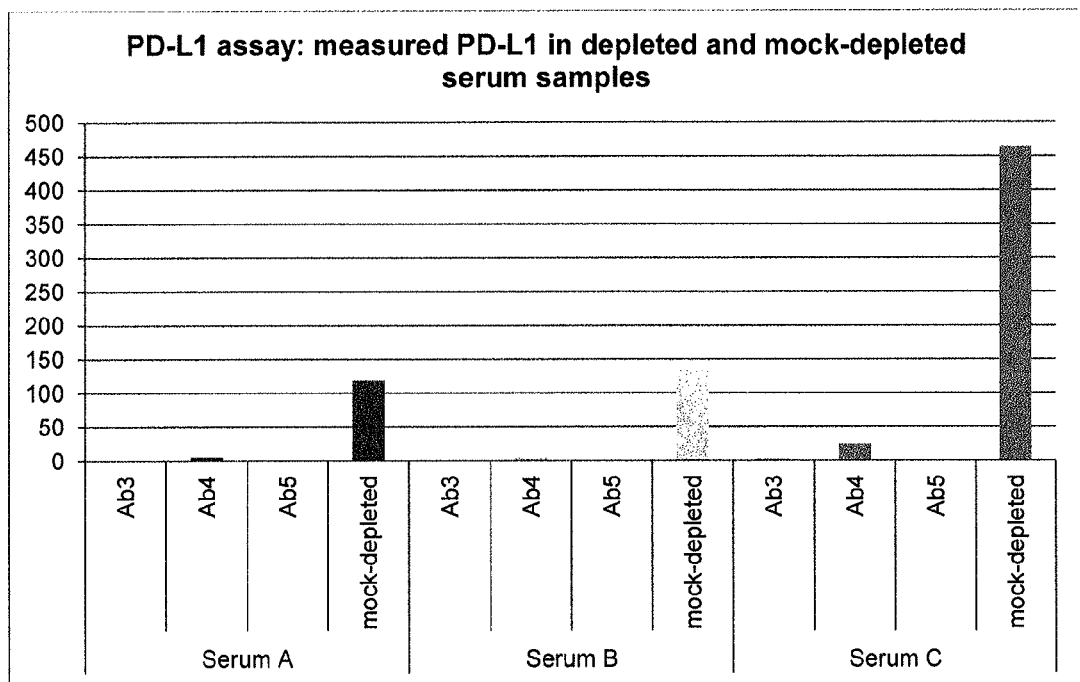
FIG. 5 illustrates the specificity of an ECL sandwich immunoassay of the invention for sPD-L1.

(Ab5) and Ab4, which failed to pair with 22C3 or 5F9 in the initial screen. Control aliquots of each diluted serum were mock-depleted with agarose beads that were not coupled to an antibody. As shown in FIG. 5, beads that were coupled to any of these Abs depleted most or all of the soluble PD-L1 in each of test samples A, B and C.

Example 3

Comparison of ECL Sandwich Immunoassay for sPD-L1 with Other PD-L1 Assays

Figure 6A:
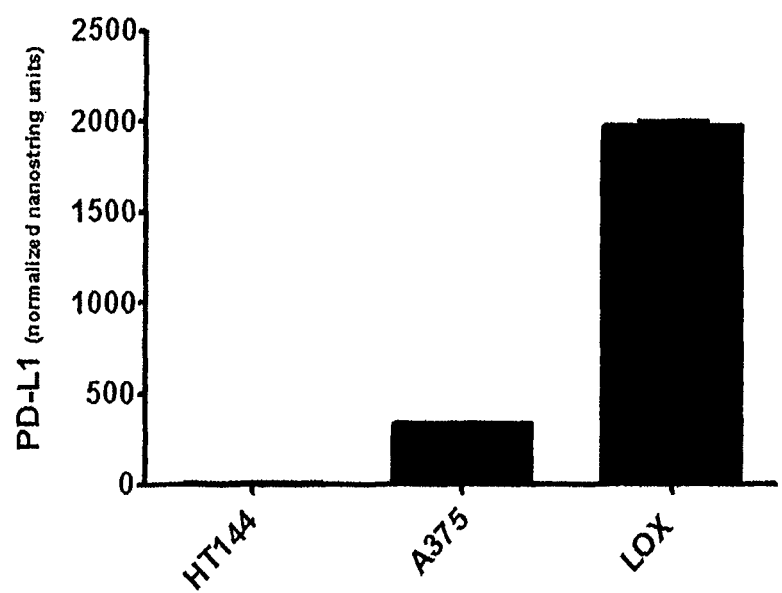
FIG. 6A, FIG. 6B, and FIG. 6C illustrate PD-L1 expression by several melanoma cancer cell lines as measured with a PD-L1 mRNA assay (FIG. 6A), a FACS assay (FIG. 6B) and an ICH assay (FIG. 6C).
Figure 6B:
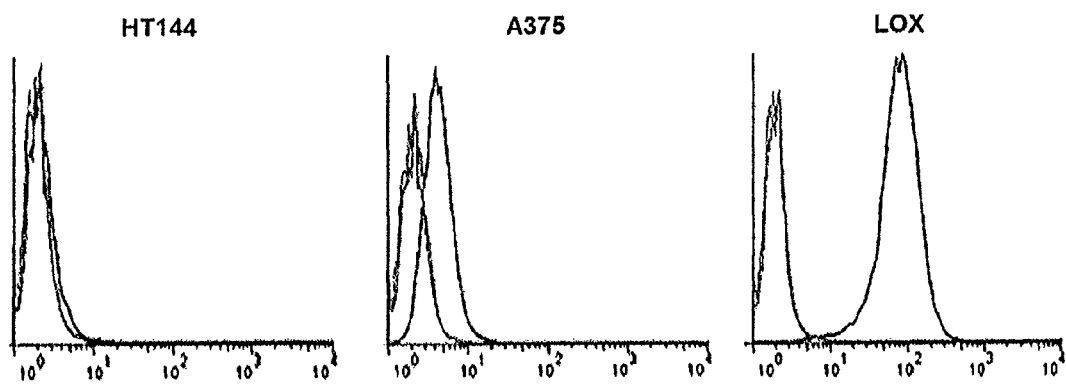
Figure 6C:
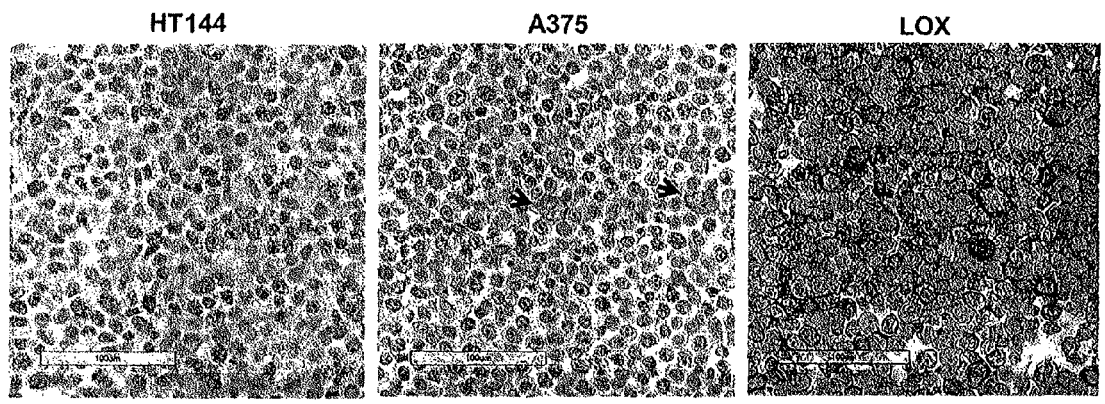

To assess the utility of sandwich ECL immunoassay using the 22C3:5F9 matched pair, the assay was used to quantify sPD-L1 in culture supernatants of several cancer cell lines, including three melanoma cell lines that had been shown to have no/low (HT144 cell line), medium (A375 cell line) or high expression (LOX cell line) of PD-L1 as measured by measuring PD-L1 mRNA or by measuring cell-surface PD-L1 protein by flow cytometric assay and IHC assay. The concentrations of sPD-L1 measured in the ECL sandwich assay are shown in Table 6 below, and the data obtained with the other assays are shown in FIGS. 6A-6C.

TABLE 6

Concentration of sPD-L1 in tumor cell line cultures.

| | Final sPD-L1 (pg/mL) after adjusting dilution factors* | | |
|---|---|---|---|
| Sample | Neat | 5X | 20X |
| Culture medium | 0.0 | 0.0 | 0.0 |
| MDA-MB-231 (breast cancer) | 75.7 | 90.3 | 89.0 |
| DU145 (prostate cancer) | 55.0 | 61.8 | 58.6 |
| HT144 (melanoma) | 2.5 | 1.0 | 0.0 |
| A375 (melanoma) | 40.2 | 43.0 | 42.3 |
| Lox (melanoma) | 192.2 | 211.4 | 221.6 |

*LLOQ = 1.5 pg/mL

Example 4

Optimization of Capture Antibody Concentration

The inventors conducted experiments to assess the ability of the immunoassay using three different concentrations of biotinylated 22C3 (0.5, 1 and 2 micrograms/ml) to accurately quantitate sPD-L1.

Figure 7:
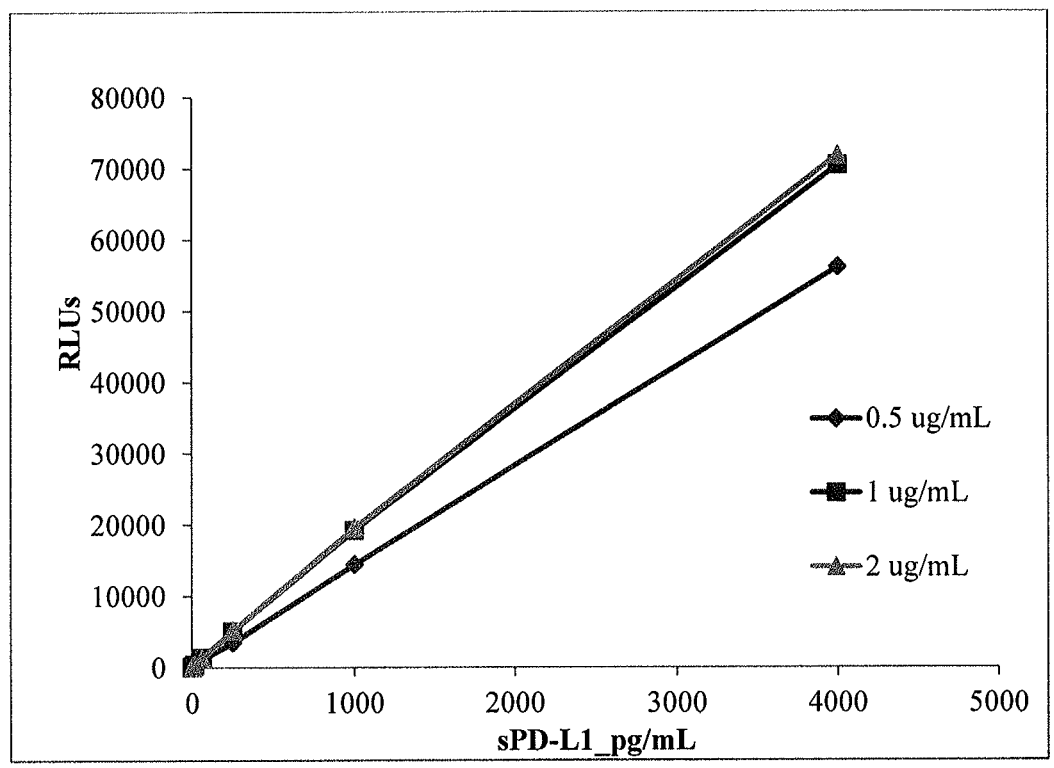
FIG. 7 illustrates the effect of different concentrations of a preferred capture antibody on the quantitation of sPD-L1 standards using an immunoassay of the invention.

In one experiment, known standards covering 3.9 to 4,000 pg/ml were assayed and the results are shown in Table 7 below and in FIG. 7.

TABLE 7

Effect of capture antibody concentration on sPD-L1 quantitation in standards.

| | Capture antibody concentration | | |
|---|---|---|---|
| Calibrators (pg/mL) | 0.5 ug/mL Ave. RLUs | 1 ug/mL Ave. RLUs | 2 ug/mL Ave. RLUs |
| 4000 | 56228 | 70496 | 71906 |
| 1000 | 14424 | 19227 | 19597 |
| 250 | 3461 | 5073 | 5187 |
| 62.5 | 1056 | 1359 | 1204 |
| 15.6 | 339 | 401 | 360 |
| 3.9 | 111 | 136 | 135 |
| 0 | 34 | 37 | 33 |

Figure 8:
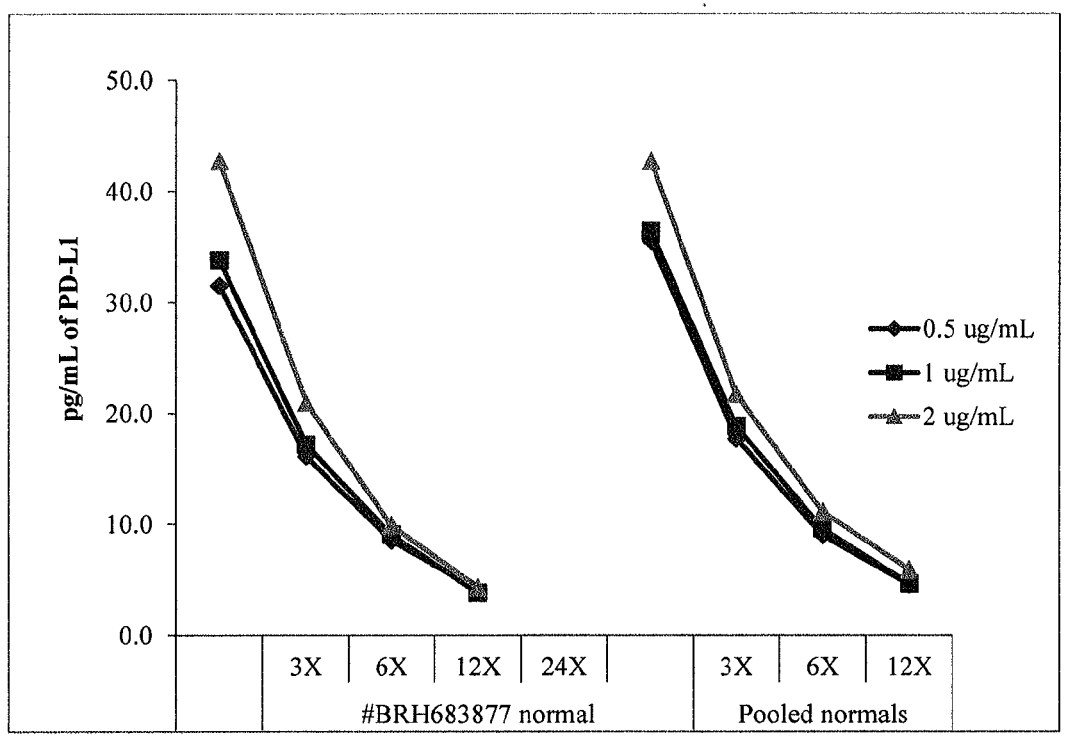
FIG. 8 illustrates the effect of different concentrations of a preferred capture antibody on the quantitation of sPD-L1 in serial dilutions of patient serum samples using an immunoassay of the invention.

In another experiment, serial dilutions of clinical samples were assayed and the results are shown in Table 8 below and in FIG. 8.

TABLE 8

Effect of capture antibody concentration on sPD-L1 quantitation in clinical samples.

| | | Back-calculated sPD-L1 (pg/mL) Capture antibody concentration | | |
|---|---|---|---|---|
| Sample | Dilution Factor | 0.5 ug/mL | 1 ug/mL | 2 ug/mL |
| #BRH683877 normal | 3X | 31.5 | 33.8 | 42.7 |
| | 6X | 16.1 | 17.2 | 20.9 |
| | 12X | 8.5 | 9.0 | 9.9 |
| | 24X | 4.1 | 3.8 | 4.3 |
| Pooled normal | 3X | 35.5 | 36.4 | 42.7 |
| | 6X | 17.7 | 18.8 | 21.7 |
| | 12X | 9.0 | 9.6 | 11.1 |
| | 24X | 4.6 | 4.6 | 5.9 |

Example 5

Optimization of Detector Antibody Concentration

The inventors also conducted experiments to assess the ability of the immunoassay using 2 micrograms/ml of biotinylated Ab 22C3 as the capture Ab and one of three different concentrations of labeled antibody 5F9 (1, 2 or 4 micrograms/ml) to accurately quantitate sPD-L1.

Figure 9:
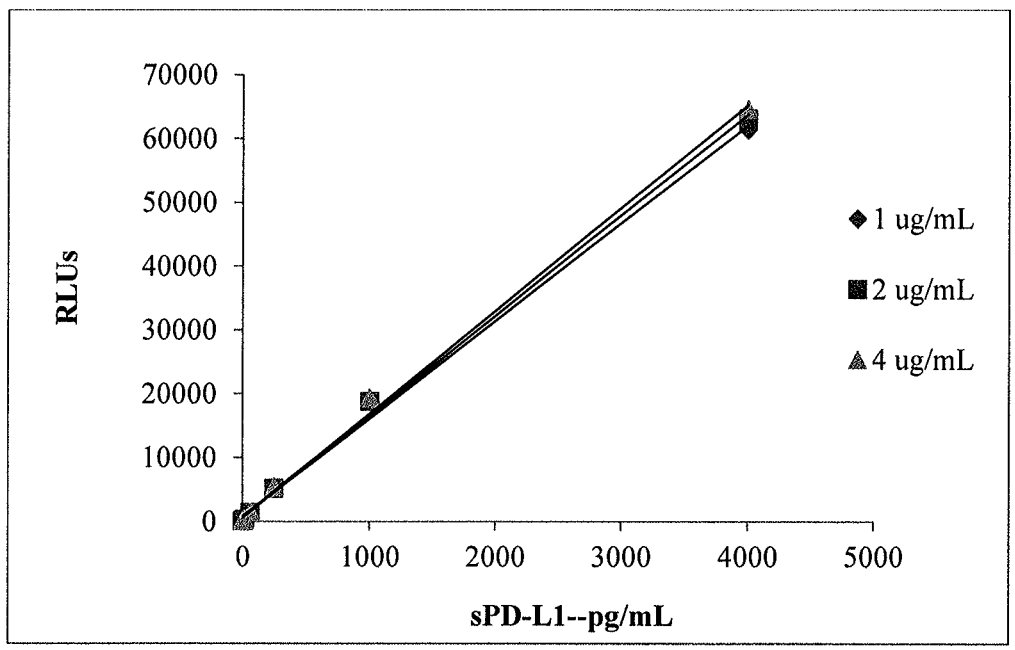
FIG. 9 illustrates the effect of different concentrations of a preferred detector antibody on the quantitation of sPD-L1 standards using an immunoassay of the invention.

In one experiment, known standards covering 3.9 to 4,000 pg/ml were assayed and the results are shown in Table 9 below and in FIG. 9.

TABLE 9

Effect of detector antibody concentration on sPD-L1 quantitation in standards.

| | Detector antibody concentration | | |
|---|---|---|---|
| Calibrators (pg/mL) | 1 ug/mL Ave. RLUs | 2 ug/mL Ave. RLUs | 4 ug/mL Ave. RLUs |
| 4000 | 61431 | 63193 | 64677 |
| 1000 | 18806 | 18848 | 19321 |
| 250 | 5195 | 5191 | 5440 |
| 62.5 | 1434 | 1392 | 1488 |
| 15.625 | 330 | 327 | 341 |
| 3.90625 | 119 | 127 | 136 |
| 0 | 31 | 37 | 43 |

Figure 10:
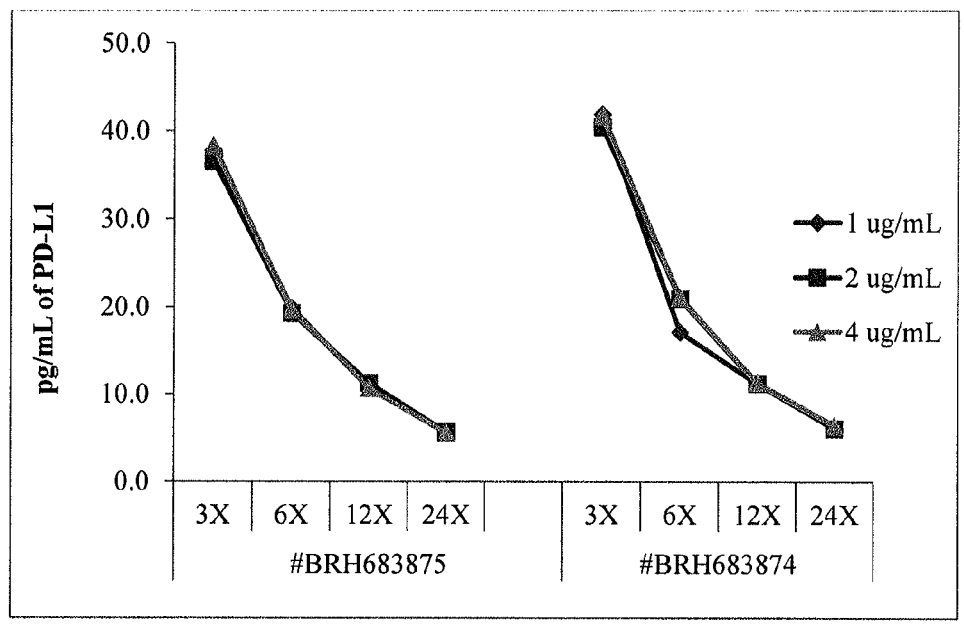
FIG. 10 illustrates the effect of different concentrations of a preferred detector antibody on the quantitation of sPD-L1 in serial dilutions of patient serum samples using an immunoassay of the invention.

In another experiment, serial dilutions of different clinical samples were assayed and the results are shown in Table 10 below and in FIG. 10.

TABLE 10

Effect of detector antibody concentration on sPD-L1 quantitation in clinical samples.

| | | Back-calculated sPD-L1 (pg/mL) Detector antibody concentration | | |
|---|---|---|---|---|
| Sample | Dilution Factor | 1 ug/mL | 2 ug/mL | 4 ug/mL |
| #BRH683875 | 3X | 37.8 | 36.6 | 38.4 |
| | 6X | 19.9 | 19.3 | 19.7 |
| | 12X | 10.7 | 11.3 | 10.7 |
| | 24X | 5.6 | 5.7 | 5.5 |

TABLE 10-continued

Effect of detector antibody concentration on sPD-L1 quantitation in clinical samples.

| Sample | Dilution Factor | Back-calculated sPD-L1 (pg/mL) Detector antibody concentration | | |
|---|---|---|---|---|
| | | 1 ug/mL | 2 ug/mL | 4 ug/mL |
| #BRH683874 | 3X | 41.9 | 40.4 | 41.8 |
| | 6X | 17.1 | 21.0 | 21.1 |
| | 12X | 11.2 | 11.2 | 11.4 |
| | 24X | 6.2 | 6.1 | 6.5 |

Example 6

Suitability of Assay for Quantitating sPD-L1 in Subjects Treated with a PD-1 Antagonist Most of the PD-1 antagonists under development for the treatment of cancer are monoclonal antibodies that block the interaction between PD-L1 and PD-1. Thus, the inventors investigated whether the accuracy of sPD-L1 measurement is affected in samples from patients treated with MK-3475. Standard curves of standards containing known sPD-L1 concentrations were generated in the presence and absence of MK-3475 and then the standard curve signals and recovery were compared. The sPD-L1 concentrations in the standards were 1.1, 3.3, 9.9, 29.6, 88.9, 266.7, 800 or 2400 pg/ml and the concentrations used for MK-3475 were based on Cmax (maximum concentration of drug achieved in blood) determined in clinical trial subjects after injection of 10 mg/kg and 2 mg/kg doses. These Cmax values were found to be ~400 µg/ml and 60 µg/ml for 10 mg/kg and 2 mg/kg, respectively in the PN001 study. Therefore, standard curves were generated with no MK-3475 or with 400 µg/ml, 200 µg/ml, or 60 µg/ml of MK-3475 added to the sPD-L1 standards.

Figure 11:
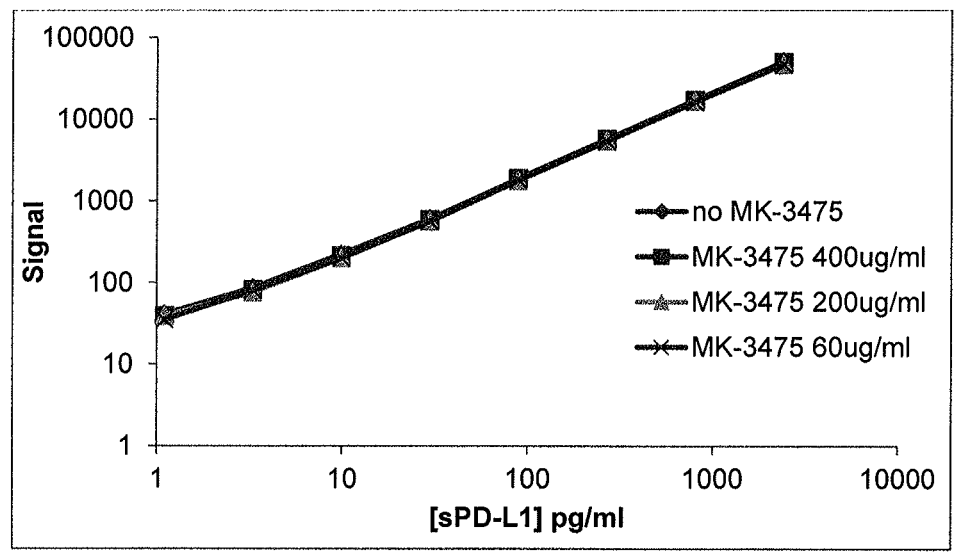
FIG. 11 shows the signals obtained using an immunoassay of the invention for samples with known sPD-L1 amounts in the presence or absence of different concentrations of the anti-PD-1 antibody MK-3475.

As shown in FIG. 11, the standard curves overlapped with insignificant changes in signal. Also, the recovery of standards obtained in the absence or presence of three different concentrations of MK-3475 were within a 80-120% range, as shown in Table 10 below.

TABLE 11

Standard recovery comparison in the presence and absence of MK-3475.

| | | MK-3475 concentration µg/ml | | |
|---|---|---|---|---|
| | Std Conc pg/ml | 0 | 400 | 200 | 60 |
| S1 | 2400 | 100 | 98 | 92 | 93 |
| S2 | 800 | 101 | 101 | 98 | 96 |
| S3 | 266.7 | 101 | 101 | 96 | 96 |
| S4 | 88.9 | 100 | 101 | 94 | 97 |
| S5 | 29.6 | 97 | 94 | 89 | 91 |
| S6 | 9.9 | 102 | 97 | 89 | 90 |
| S7 | 3.3 | 102 | 94 | 84 | 92 |
| S8 | 1.1 | 98 | 89 | 89 | 71 |

These results indicate that MK-3475 does not interfere with sPD-L1 measurement in liquid samples.

Example 7

Assay for sPD-L1 in Normal and Disease Subjects

Figure 12:
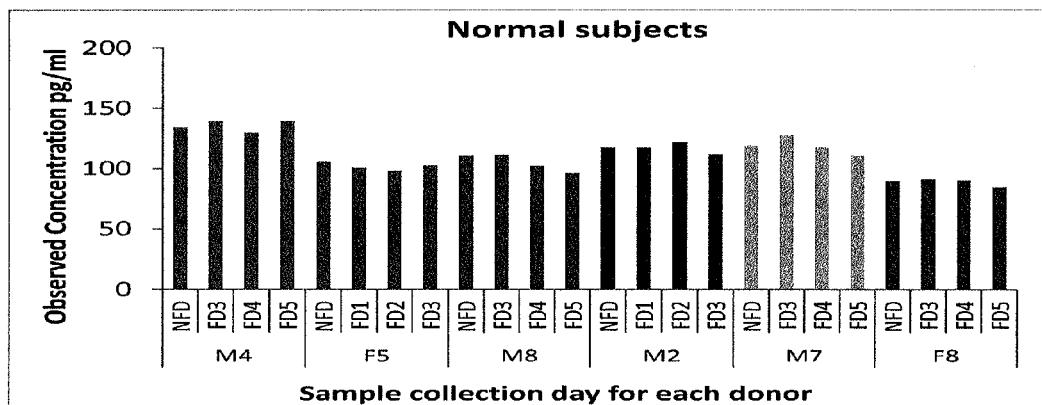
FIG. 12 illustrates the intra-patient variability of sPD-L1 levels detected in serum samples from normal subjects in fed and fasted states using an immunoassay of the invention.
Figure 13:
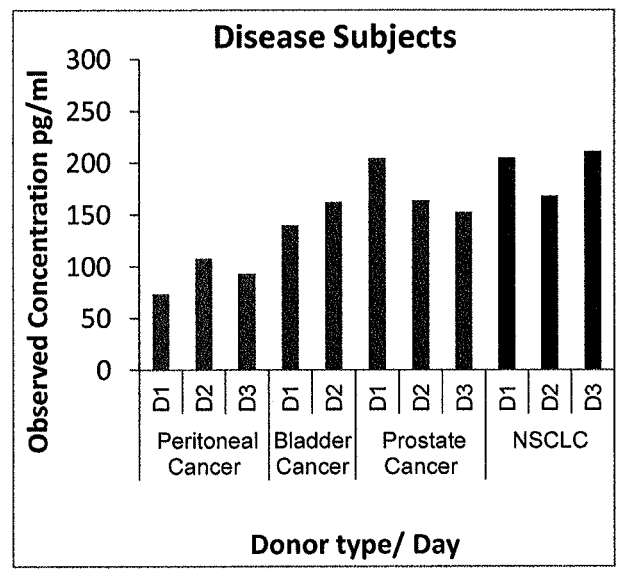
FIG. 13 illustrates the intra-patient variability of sPD-L1 levels detected in serum samples from patients with different cancer types using an immunoassay of the invention.

The inventors used a preferred embodiment of the ECL sandwich immunoassay of the invention was used to investigate the variability of sPD-L1 levels within individual subjects. In one experiment, the assay was performed on samples collected from six normal subjects in fed and fasted states, and the results are shown in FIG. 12. In another experiment, the assay was performed on serum samples from collected on three different days from subjects with four different types of cancer, and the results are shown in FIG. 13.

Figure 14:
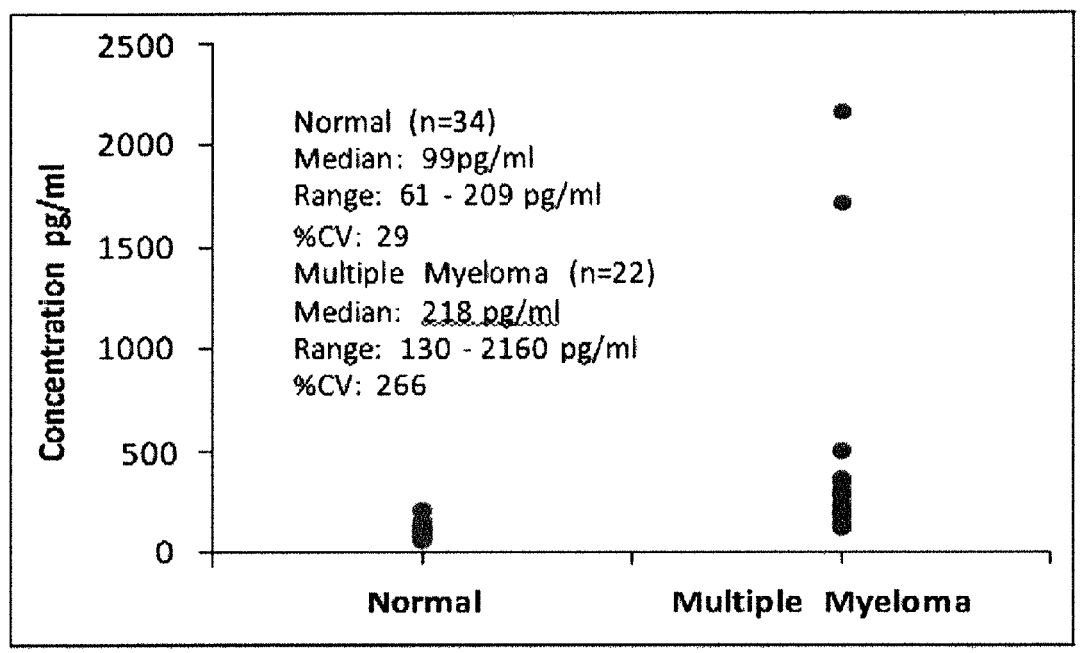
FIG. 14 illustrates the inter-patient variability of sPD-L1 levels detected in serum samples from normal subjects and patients with multiple myeloma using an immunoassay of the invention.

The inventors used the same assay to investigate the inter-subject variability of sPD-L1 levels in serum samples from 34 normal donors and 22 multiple myeloma patients. The results are shown in FIG. 14.

REFERENCES

1. Sharpe, A. H, et al., *Nature Immunology* 8:239-245 (2007).
2. Dong H., et al. *Nat Med.* 8(8):793-800 (2002).
3. Yang et al., *Invest Ophthalmol Vis Sci.* 49:2518-2525 (2008).
4. Ghebeh et al. *Neoplasia* 8: 190-198 (2006).
5. Hamanishi J., et al., *Proceeding of the National Academy of Sciences* 104: 3360-3365 (2007).
6. Nomi, T., et al., *Clinical Cancer Research* 13:2151-2157 (2007).
8. Ohigashi Y., et al., *Clin. Cancer Research* 11: 2947-2953 (2005).
9. Inman et al., *Cancer* 109: 1499-1505 (2007).
10. Shimauchi T., et al., *Int. J. Cancer* 121:2585-2590 (2007).
11. Gao et al., *Clinical Cancer Research* 15: 971-979 (2009).
12. Nakanishi J., *Cancer Immunol Immunother.* 56:1173-1182 (2007).
13. Hino et al., *Cancer* 116 (7):1757-1766 (2010).
14. Ghebeh H., *BMC Cancer.* 8:57 (2008).
15. Ahmadzadeh M et al., *Blood* 114: 1537-1544 (2009).
16. Thompson R. H. et al., *Clinical Cancer Research* 15: 1757-1761 (2007).
17. Toplian, S. L., et al., *New Eng. J Med.* 366 (26): 2443-2454 (2012).
18. Hamid, O., et al., *New Eng. J Med.* 369: 134-144 (2013).
19. Spigel, D. R., et al., *J. Clin. Oncol.* 31: Suppl, abstr 8008 (2013)
20. Thompson, R. H., et al., *PNAS* 101 (49): 17174-17179 (2004).
21. Thompson, R. H. et al., *Cancer Res.* 66: 3381-3385 (2006).
22. Gadiot, J., et al., *Cancer* 117:2192-2201 (2011).
23. Taube, J. M. et al., *Sci Transl Med* 4 (127): 127ra37 (2012).
24. Chen, Y., et al., *Cytokine* 56:231-238 (2011).
25. Frigola, X., et al., *Clin. Cancer Res.* 17:1915-1923 (2011).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. §1.57(b)(1), to relate to each and every individual publication, database entry (e.g. Genbank sequences or GeneID entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A kit for detecting soluble human Programmed Cell Death 1 Ligand 1 (shPD-L1) in a liquid sample, wherein:
   (a) the kit comprises a capture binding molecule and a detector binding molecule;
   (b) the capture reagent is an isolated antibody or antigen binding fragment thereof that specifically binds shPD-L1 and comprises three light chain CDRs of SEQ ID NOs: 7, 8 and 9 and three heavy chain CDRs of SEQ ID NOs: 13, 14 and 15; and
   (c) the detector binding molecule is an isolated antibody or antigen binding fragment thereof that is capable of specifically binding to shPD-L1 molecules that are complexed with the capture binding molecule and which comprises: (a) three light chain CDRs of SEQ ID NOs: 19, 20 and 21 and three heavy chain CDRs of SEQ ID NOs: 25, 26 and 27; or (b) three light chain CDRs of SEQ ID NOs: 31, 32 and 33 and three heavy chain CDRs of SEQ ID NOs: 37, 38 and 39.

2. The kit of claim 1, wherein the capture binding molecule is immobilized on a solid support and the detector binding molecule comprises a detectable label.

3. The kit of claim 2, wherein the capture binding molecule is biotinylated.

4. The kit of claim 1, wherein the detector binding molecule is labeled with an amine reactive, N-hydroxysuccinimide ester.

5. The kit of claim 1, wherein the kit comprises a solid support that is coated with streptavidin.

6. The kit of claim 1, wherein the capture binding molecule is an antibody which comprises a light chain variable region of SEQ ID NO:1 and a heavy chain variable region of SEQ ID NO:2.

7. The kit of claim 1, wherein the detector binding molecule is an antibody which comprises:
   (a) a light chain variable region of SEQ ID NO:3 and a heavy chain variable region of SEQ ID NO:4; or
   (b) a light chain variable region of SEQ ID NO:5 and a heavy chain variable region of SEQ ID NO:6.

8. The kit of claim 1, wherein the detector binding molecule is an antibody which comprises a light chain variable region of SEQ ID NO:3 and a heavy chain variable region of SEQ ID NO:4.

9. An assay for detecting sPD-L1 in a liquid sample which comprises:
   (a) providing a solid substrate that is coated with a capture binding molecule, wherein the capture binding molecule is an isolated antibody or antigen binding fragment thereof that specifically binds sPD-L1 and comprises three light chain CDRs of SEQ ID NOs: 7, 8 and 9 and three heavy chain CDRs of SEQ ID NOs: 13, 14 and 15;
   (b) incubating the sample with the solid substrate under conditions suitable for formation of a first complex between the capture binding molecule and sPD-L1 in the sample,
   (c) washing the solid substrate at least once with a wash buffer to remove the unbound sPD-L1,
   (d) incubating the solid substrate with a detector binding molecule under conditions suitable for formation of a second complex between the captured sPD-L1 and the detector binding molecule, wherein the detector binding molecule is an isolated antibody or antigen binding fragment thereof that is capable of specifically binding to shPD-L1 molecules that are complexed with the capture binding molecule and which comprises: (i) three light chain CDRs of SEQ ID NOs: 19, 20 and 21 and three heavy chain CDRs of SEQ ID NOs: 25, 26 and 27; or (ii) three light chain CDRs of SEQ ID NOs: 31, 32 and 33 and three heavy chain CDRs of SEQ ID NOs: 37, 38 and 39;
   (e) washing the solid substrate at least once with the wash buffer to remove the unbound detector binding molecule, and
   (f) detecting the second complex.

10. The assay of claim 9, wherein the capture binding molecule is biotinylated and the solid substrate is coated with streptavidin or avidin.

11. The assay of claim 9, wherein the capture binding molecule is biotinylated and the solid substrate is a 96 well microtiter plate coated with streptavidin.

12. The assay of claim 9, wherein the detector binding molecule is labeled with an amine reactive, N-hydroxysuccinimide ester.

13. The assay of claim 9, wherein the capture binding molecule is an antibody which comprises a light chain variable region of SEQ ID NO:1 and a heavy chain variable region of SEQ ID NO:2 and the detector binding molecule is an antibody which comprises a light chain variable region of SEQ ID NO:3 and a heavy chain variable region of SEQ ID NO:4.

14. The assay of claim 9, wherein the assay comprises assaying a set of standards having sPD-L1 concentrations of about 1.1 pg/ml, 3.3 pg/ml, 9.9 pg/ml, 29.6 pg/ml, 88.9 pg/ml, 266.7 pg/ml, 800 pg/ml and 2400 pg/ml.

15. The assay of claim 9, wherein the liquid sample comprises serum or plasma prepared from a blood sample removed from a subject with a cancer.

16. The assay of claim 15, wherein the liquid sample is a four-fold dilution of the serum or plasma preparation.

17. The assay of claim 15, wherein the cancer is multiple myeloma.

* * * * *

SEQUENCE LISTING

```
<160> NUMBER OF SEQ ID NOS: 42

<210> SEQ ID NO 1
<211> LENGTH: 112
<212> TYPE: PRT
<213> ORGANISM: Mus musculus

<400> SEQUENCE: 1

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Leu His Thr
                20                  25                  30

Ser Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Val Val Thr Phe Gly Ala Gly Thr Lys Leu Glu Leu Lys
                100                 105                 110

<210> SEQ ID NO 2
<211> LENGTH: 122
<212> TYPE: PRT
<213> ORGANISM: Mus musculus

<400> SEQUENCE: 2

Gln Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Trp Ile His Trp Ile Lys Gln Arg Pro Gly Gln Gly Leu Glu Trp Ile
            35                  40                  45

Gly Tyr Ile Asn Pro Ser Ser Gly Tyr His Glu Tyr Asn Gln Lys Phe
        50                  55                  60

Ile Asp Lys Ala Thr Leu Thr Ala Asp Arg Ser Ser Ser Thr Ala Tyr
65                  70                  75                  80

Met His Leu Thr Ser Leu Thr Ser Glu Asp Ser Ala Val Tyr Tyr Cys
                85                  90                  95

Ala Arg Ser Gly Trp Leu Ile His Gly Asp Tyr Tyr Phe Asp Phe Trp
                100                 105                 110

Gly Gln Gly Thr Thr Leu Thr Val Ser Ser
            115                 120

<210> SEQ ID NO 3
<211> LENGTH: 107
<212> TYPE: PRT
```

<213> ORGANISM: Mus musculus

<400> SEQUENCE: 3

```
Asp Ile Val Met Thr Gln Ser His Lys Phe Met Ser Thr Ser Val Gly
  1               5                  10                  15
Asp Arg Val Ser Ile Thr Cys Lys Ala Ser Gln Asp Val Ser Thr Ala
             20                  25                  30
Val Ala Trp Tyr Gln Gln Lys Pro Gly Gln Ser Pro Lys Leu Leu Ile
         35                  40                  45
Tyr Trp Ala Ser Thr Arg His Thr Gly Val Pro Asp Arg Phe Thr Gly
     50                  55                  60
Ser Ala Ser Gly Ile Asp Phe Thr Leu Thr Ile Ser Ser Leu Gln Ala
 65                  70                  75                  80
Glu Asp Leu Ala Leu Tyr Tyr Cys Gln Gln His Tyr Arg Thr Pro Trp
                 85                  90                  95
Thr Phe Gly Gly Gly Thr Lys Leu Glu Ile Lys
            100                 105
```

<210> SEQ ID NO 4
<211> LENGTH: 120
<212> TYPE: PRT
<213> ORGANISM: Mus musculus

<400> SEQUENCE: 4

```
Glu Val His Leu Gln Gln Ser Gly Pro Glu Leu Val Lys Pro Gly Ala
  1               5                  10                  15
Ser Val Lys Ile Ser Cys Lys Ala Ser Gly Ala Pro Phe Thr Asp Phe
             20                  25                  30
Asn Ile His Trp Met Lys Gln Ser His Gly Gly Ser Leu Glu Trp Ile
         35                  40                  45
Gly Ser Ile Tyr Pro Tyr Asn Gly Asn Thr Asn Tyr Asn Gln Lys Phe
     50                  55                  60
Lys Asn Lys Ala Thr Leu Thr Val Asp Asp Ser Ser Ile Thr Ala Tyr
 65                  70                  75                  80
Met Glu Phe Arg Ser Leu Thr Ser Glu Asp Ser Ala Phe Tyr Tyr Cys
                 85                  90                  95
Ala Arg Gly Tyr Ile Val Thr Thr Ala Trp Phe Ala Tyr Trp Gly Gln
            100                 105                 110
Gly Thr Leu Val Thr Val Ser Ala
        115                 120
```

<210> SEQ ID NO 5
<211> LENGTH: 108
<212> TYPE: PRT
<213> ORGANISM: Mus musculus

<400> SEQUENCE: 5

```
Glu Ile Val Leu Thr Gln Ser Pro Ala Leu Met Ala Ala Ser Pro Gly
  1               5                  10                  15
Glu Lys Val Thr Ile Thr Cys Ser Val Ser Ser Ser Ile Ser Ser Ser
             20                  25                  30
Asn Leu His Trp Tyr Gln Gln Lys Ser Glu Thr Ser Pro Lys Pro Trp
         35                  40                  45
Ile Tyr Gly Thr Ser Asn Leu Ala Ser Gly Val Pro Val Arg Phe Ser
     50                  55                  60
Gly Ser Gly Ser Gly Thr Ser Tyr Ser Leu Thr Ile Ser Ser Met Glu
 65                  70                  75                  80
```

```
Ala Glu Asp Ala Ala Thr Tyr Tyr Cys Gln Gln Trp Ser Ser Tyr Pro
                85                  90                  95

Leu Thr Phe Gly Ser Gly Thr Lys Leu Glu Ile Lys
            100                 105

<210> SEQ ID NO 6
<211> LENGTH: 121
<212> TYPE: PRT
<213> ORGANISM: Mus musculus

<400> SEQUENCE: 6

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Lys Met Tyr Trp Val Lys Gln Ser His Gly Lys Ser Leu Glu Trp Ile
        35                  40                  45

Gly Tyr Ile Asp Pro Tyr Asn Gly Gly Ile Asn Tyr Asn Gln Met Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Ala Lys Gln Asp Met Pro Pro Pro Trp Phe Val Tyr Trp Gly
            100                 105                 110

Gln Gly Thr Leu Val Thr Val Ser Ala
        115                 120

<210> SEQ ID NO 7
<211> LENGTH: 17
<212> TYPE: PRT
<213> ORGANISM: Mus musculus

<400> SEQUENCE: 7

Lys Ser Ser Gln Ser Leu Leu His Thr Ser Thr Arg Lys Asn Tyr Leu
1               5                   10                  15

Ala

<210> SEQ ID NO 8
<211> LENGTH: 7
<212> TYPE: PRT
<213> ORGANISM: Mus musculus

<400> SEQUENCE: 8

Trp Ala Ser Thr Arg Glu Ser
1               5

<210> SEQ ID NO 9
<211> LENGTH: 8
<212> TYPE: PRT
<213> ORGANISM: Mus musculus

<400> SEQUENCE: 9

Lys Gln Ser Tyr Asp Val Val Thr
1               5

<210> SEQ ID NO 10
<211> LENGTH: 20
<212> TYPE: PRT
<213> ORGANISM: Mus musculus
```

<400> SEQUENCE: 10

Met Asp Ser Gln Ala Gln Val Leu Ile Leu Leu Leu Trp Val Ser
1               5                   10                  15

Gly Thr Cys Gly
            20

<210> SEQ ID NO 11
<211> LENGTH: 132
<212> TYPE: PRT
<213> ORGANISM: Mus musculus

<400> SEQUENCE: 11

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Thr Cys Lys Ser Ser Gln Ser
        35                  40                  45

Leu Leu His Thr Ser Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asp Val Val Thr Phe Gly Ala Gly Thr Lys
        115                 120                 125

Leu Glu Leu Lys
    130

<210> SEQ ID NO 12
<211> LENGTH: 396
<212> TYPE: DNA
<213> ORGANISM: Mus musculus

<400> SEQUENCE: 12
atggattcac aggcccaggt tcttatattg ctgctgctat gggtatctgg tacctgtggg      60
gacattgtga tgtcacagtc tcctcctcc ctggctgtgt cagcaggaga gaaggtcact     120
atgacctgca atccagtca gagtctgctc cacactagca cccgaaagaa ctacttggct     180
tggtaccagc agaaaccagg gcagtctcct aaactgctga tctattgggc atccactagg    240
gaatctgggg tccctgatcg cttcacaggc agtggatctg gacagatttt cactctcacc    300
atcagcagtg tgcaggctga agacctggca gtttattact gcaaacaatc ttatgatgtg    360
gtcacgttcg gtgctgggac caagctggag ctgaaa                              396

<210> SEQ ID NO 13
<211> LENGTH: 5
<212> TYPE: PRT
<213> ORGANISM: Mus musculus

<400> SEQUENCE: 13

Ser Tyr Trp Ile His
1               5

<210> SEQ ID NO 14

<211> LENGTH: 17
<212> TYPE: PRT
<213> ORGANISM: Mus musculus

<400> SEQUENCE: 14

Tyr Ile Asn Pro Ser Ser Gly Tyr His Glu Tyr Asn Gln Lys Phe Ile
1               5                   10                  15
Asp

<210> SEQ ID NO 15
<211> LENGTH: 13
<212> TYPE: PRT
<213> ORGANISM: Mus musculus

<400> SEQUENCE: 15

Ser Gly Trp Leu Ile His Gly Asp Tyr Tyr Phe Asp Phe
1               5                   10

<210> SEQ ID NO 16
<211> LENGTH: 19
<212> TYPE: PRT
<213> ORGANISM: Mus musculus

<400> SEQUENCE: 16

Met Glu Arg His Trp Ile Phe Leu Phe Leu Phe Ser Val Thr Ala Gly
1               5                   10                  15
Val His Ser

<210> SEQ ID NO 17
<211> LENGTH: 141
<212> TYPE: PRT
<213> ORGANISM: Mus musculus

<400> SEQUENCE: 17

Met Glu Arg His Trp Ile Phe Leu Phe Leu Phe Ser Val Thr Ala Gly
1               5                   10                  15

Val His Ser Gln Val His Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Ser Tyr Trp Ile His Trp Ile Lys Gln Arg Pro Gly Gln Gly Leu
    50                  55                  60

Glu Trp Ile Gly Tyr Ile Asn Pro Ser Ser Gly Tyr His Glu Tyr Asn
65                  70                  75                  80

Gln Lys Phe Ile Asp Lys Ala Thr Leu Thr Ala Asp Arg Ser Ser Ser
                85                  90                  95

Thr Ala Tyr Met His Leu Thr Ser Leu Thr Ser Glu Asp Ser Ala Val
            100                 105                 110

Tyr Tyr Cys Ala Arg Ser Gly Trp Leu Ile His Gly Asp Tyr Tyr Phe
        115                 120                 125

Asp Phe Trp Gly Gln Gly Thr Thr Leu Thr Val Ser Ser
    130                 135                 140

<210> SEQ ID NO 18
<211> LENGTH: 423
<212> TYPE: DNA
<213> ORGANISM: Mus musculus

<400> SEQUENCE: 18
atggaaaggc actggatctt tctcttcctg ttttcagtaa ctgcaggtgt ccactcccag      60

```
gtccaccttc agcagtctgg ggctgaactg gcaaaacctg gggcctcagt gaagatgtcc      120
tgcaaggctt ctggctacac gtttactagt tactggatac actggataaa gcagaggcct      180
ggacagggtc tggaatggat tggatacatt aatccttcct ctggttatca tgaatacaat      240
cagaaattca ttgacaaggc cacattgact gctgacagat cctccagcac agcctacatg      300
cacctgacca gcctgacgtc tgaagactct gcagtctatt actgtgcaag atcgggatgg      360
ttaatacatg gagactacta ctttgacttc tggggccaag gcaccactct cacagtctcc      420
tca                                                                    423
```

<210> SEQ ID NO 19
<211> LENGTH: 11
<212> TYPE: PRT
<213> ORGANISM: Mus musculus

<400> SEQUENCE: 19

Lys Ala Ser Gln Asp Thr Ser Thr Ala Val Ala
1               5                   10

<210> SEQ ID NO 20
<211> LENGTH: 7
<212> TYPE: PRT
<213> ORGANISM: Mus musculus

<400> SEQUENCE: 20

Trp Ala Ser Thr Arg His Thr
1               5

<210> SEQ ID NO 21
<211> LENGTH: 9
<212> TYPE: PRT
<213> ORGANISM: Mus musculus

<400> SEQUENCE: 21

Gln Gln His Tyr Arg Thr Pro Trp Thr
1               5

<210> SEQ ID NO 22
<211> LENGTH: 20
<212> TYPE: PRT
<213> ORGANISM: Mus musculus

<400> SEQUENCE: 22

Met Glu Ser Gln Ile Gln Ala Phe Val Phe Val Leu Leu Trp Leu Ser
1               5                   10                  15

Gly Val Asp Gly
            20

<210> SEQ ID NO 23
<211> LENGTH: 127
<212> TYPE: PRT
<213> ORGANISM: Mus musculus

<400> SEQUENCE: 23

Met Glu Ser Gln Ile Gln Ala Phe Val Phe Val Leu Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Thr Ser Thr Ala Val Ala Trp Tyr Gln Gln Lys Pro Gly Gln Ser Pro
 50                  55                  60

Lys Leu Leu Ile Tyr Trp Ala Ser Thr Arg His Thr Gly Val Pro Asp
 65                  70                  75                  80

Arg Phe Thr Gly Ser Ala Ser Gly Ile Asp Phe Thr Leu Thr Ile Ser
                 85                  90                  95

Ser Leu Gln Ala Glu Asp Leu Ala Leu Tyr Tyr Cys Gln Gln His Tyr
                100                 105                 110

Arg Thr Pro Trp Thr Phe Gly Gly Gly Thr Lys Leu Glu Ile Lys
            115                 120                 125

<210> SEQ ID NO 24
<211> LENGTH: 381
<212> TYPE: DNA
<213> ORGANISM: Mus musculus

<400> SEQUENCE: 24
atggagtcac agattcaggc atttgtattc gtgcttctct ggttgtctgg tgttgacgga     60
gacattgtta tgacccagtc tcacaaattc atgtccacat cagtaggaga cagggtcagc    120
atcacctgca aggccagtca ggatactagt actgctgtag cctggtatca acaaaaacca    180
gggcaatctc ctaaactact gatttactgg gcatccaccc ggcacactgg agtccctgat    240
cgcttcacag gcagtgcatc tggaatagat tttactctca ccatcagcag tttgcaggct    300
gaagacctgg cactttatta ttgtcagcaa cattatagaa ctccgtggac gttcggtgga    360
ggcaccaagc tggagatcaa a                                              381

<210> SEQ ID NO 25
<211> LENGTH: 5
<212> TYPE: PRT
<213> ORGANISM: Mus musculus

<400> SEQUENCE: 25

Asp Phe Asn Ile His
 1               5

<210> SEQ ID NO 26
<211> LENGTH: 17
<212> TYPE: PRT
<213> ORGANISM: Mus musculus

<400> SEQUENCE: 26

Ser Ile Tyr Pro Tyr Asn Gly Asn Thr Asn Tyr Asn Gln Lys Phe Lys
 1               5                  10                  15

Asn

<210> SEQ ID NO 27
<211> LENGTH: 11
<212> TYPE: PRT
<213> ORGANISM: Mus musculus

<400> SEQUENCE: 27

Gly Tyr Ile Val Thr Thr Ala Trp Phe Ala Tyr
 1               5                  10

<210> SEQ ID NO 28
<211> LENGTH: 19
<212> TYPE: PRT
<213> ORGANISM: Mus musculus

<400> SEQUENCE: 28

Met Gly Trp Ser Trp Ile Phe Leu Phe Leu Leu Ser Gly Thr Ala Gly
1               5                   10                  15

Val His Ser

<210> SEQ ID NO 29
<211> LENGTH: 139
<212> TYPE: PRT
<213> ORGANISM: Mus musculus

<400> SEQUENCE: 29

Met Gly Trp Ser Trp Ile Phe Leu Phe Leu Leu Ser Gly Thr Ala Gly
1               5                   10                  15

Val His Ser Glu Val His Leu Gln Gln Ser Gly Pro Glu Leu Val Lys
            20                  25                  30

Pro Gly Ala Ser Val Lys Ile Ser Cys Lys Ala Ser Gly Ala Pro Phe
        35                  40                  45

Thr Asp Phe Asn Ile His Trp Met Lys Gln Ser His Gly Gly Ser Leu
    50                  55                  60

Glu Trp Ile Gly Ser Ile Tyr Pro Tyr Asn Gly Asn Thr Asn Tyr Asn
65                  70                  75                  80

Gln Lys Phe Lys Asn Lys Ala Thr Leu Thr Val Asp Asp Ser Ser Ile
                85                  90                  95

Thr Ala Tyr Met Glu Phe Arg Ser Leu Thr Ser Glu Asp Ser Ala Phe
            100                 105                 110

Tyr Tyr Cys Ala Arg Gly Tyr Ile Val Thr Thr Ala Trp Phe Ala Tyr
        115                 120                 125

Trp Gly Gln Gly Thr Leu Val Thr Val Ser Ala
    130                 135

<210> SEQ ID NO 30
<211> LENGTH: 417
<212> TYPE: DNA
<213> ORGANISM: Mus musculus

<400> SEQUENCE: 30
atgggatgga gctggatctt tctcttcctc ttgtcaggaa ctgcaggcgt ccactctgag     60
gtccaccttc agcagtcagg acctgaactg gtgaaacctg gggcctcagt gaagatatcc    120
tgcaaggctt ctggtgcccc attcactgac ttcaacatcc actggatgaa acagagccat    180
ggcgggagcc ttgagtggat tggatctatt tatccttaca tggaaatac taactacaac    240 cagaagttca gaacaaggc cacattgact gtggacgatt cctccatcac agcctacatg    300
gagttccgca gcctgacatc tgaggactct gcattctatt actgtgcaag aggctatatt    360
gttacgactg cctggtttgc ttattggggc caagggactc tggtcactgt ctctgca       417

<210> SEQ ID NO 31
<211> LENGTH: 12
<212> TYPE: PRT
<213> ORGANISM: Mus musculus

<400> SEQUENCE: 31

Ser Val Ser Ser Ser Ile Ser Ser Asn Leu His
1               5                   10

<210> SEQ ID NO 32
<211> LENGTH: 7
<212> TYPE: PRT
<213> ORGANISM: Mus musculus

```
<400> SEQUENCE: 32

Gly Thr Ser Asn Leu Ala Ser
1               5

<210> SEQ ID NO 33
<211> LENGTH: 9
<212> TYPE: PRT
<213> ORGANISM: Mus musculus

<400> SEQUENCE: 33

Gln Gln Trp Ser Ser Tyr Pro Leu Thr
1               5

<210> SEQ ID NO 34
<211> LENGTH: 22
<212> TYPE: PRT
<213> ORGANISM: Mus musculus

<400> SEQUENCE: 34

Met Asp Phe His Val Gln Ile Phe Ser Phe Met Leu Ile Ser Val Thr
1               5                   10                  15

Val Ile Leu Ser Ser Gly
            20

<210> SEQ ID NO 35
<211> LENGTH: 130
<212> TYPE: PRT
<213> ORGANISM: Mus musculus

<400> SEQUENCE: 35

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Tyr Gln Gln Lys Ser Glu
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ser Gly Thr Lys Leu Glu
        115                 120                 125

Ile Lys
    130

<210> SEQ ID NO 36
<211> LENGTH: 390
<212> TYPE: DNA
<213> ORGANISM: Mus musculus

<400> SEQUENCE: 36
atggattttc atgtgcagat tttcagcttc atgctaatca gtgtcacagt catattgtcc      60
agtggagaaa ttgtgctcac ccagtctcca gcactcatgg ctgcatctcc aggggagaag     120
gtcaccatca cctgcagtgt cagctcaagt ataagttcca gcaacttgca ctggtaccag     180
```

```
cagaagtcag aaacctcccc caaaccctgg atttatggca catccaacct ggcttctgga      240
gtccctgttc gcttcagtgg cagtggatct gggacctctt attctctcac aatcagcagc      300
atggaggctg aggatgctgc acttattac tgtcaacagt ggagtagtta cccactcacg       360
ttcggctcgg gacaaagtt ggaaataaaa                                        390
```

<210> SEQ ID NO 37
<211> LENGTH: 5
<212> TYPE: PRT
<213> ORGANISM: Mus musculus

<400> SEQUENCE: 37

Ser Tyr Lys Met Tyr
1               5

<210> SEQ ID NO 38
<211> LENGTH: 16
<212> TYPE: PRT
<213> ORGANISM: Mus musculus

<400> SEQUENCE: 38

Tyr Ile Asp Pro Tyr Asn Gly Gly Ile Asn Tyr Asn Gln Met Phe Lys
1               5                   10                  15

<210> SEQ ID NO 39
<211> LENGTH: 12
<212> TYPE: PRT
<213> ORGANISM: Mus musculus

<400> SEQUENCE: 39

Ala Lys Gln Asp Met Pro Pro Trp Phe Val Tyr
1               5                   10

<210> SEQ ID NO 40
<211> LENGTH: 19
<212> TYPE: PRT
<213> ORGANISM: Mus musculus

<400> SEQUENCE: 40

Met Glu Trp Arg Trp Ile Phe Leu Phe Leu Leu Ser Gly Thr Thr Gly
1               5                   10                  15

Val His Ser

<210> SEQ ID NO 41
<211> LENGTH: 140
<212> TYPE: PRT
<213> ORGANISM: Mus musculus

<400> SEQUENCE: 41

Met Glu Trp Arg Trp Ile Phe Leu Phe Leu Leu Ser Gly Thr Thr Gly
1               5                   10                  15

Val His Ser Glu Ile Gln Leu Gln Gln Ser Gly Pro Glu Leu Val Lys
            20                  25                  30

Pro Gly Ala Ser Val Lys Val Ser Cys Lys Ala Ser Gly Tyr Ala Phe
        35                  40                  45

Thr Ser Tyr Lys Met Tyr Trp Val Lys Gln Ser His Gly Lys Ser Leu
    50                  55                  60

Glu Trp Ile Gly Tyr Ile Asp Pro Tyr Asn Gly Gly Ile Asn Tyr Asn
65                  70                  75                  80

Gln Met Phe Lys Gly Lys Ala Thr Leu Thr Val Asp Lys Ser Ser Ser

```
                  85                  90                  95
Thr Ala Tyr Met His Leu Asn Ser Leu Thr Ser Glu Asp Ser Ala Val
                100                 105                 110

Tyr Tyr Cys Ala Arg Ala Lys Gln Asp Met Pro Pro Trp Phe Val
        115                 120                 125

Tyr Trp Gly Gln Gly Thr Leu Val Thr Val Ser Ala
    130                 135                 140

<210> SEQ ID NO 42
<211> LENGTH: 420
<212> TYPE: DNA
<213> ORGANISM: Mus musculus

<400> SEQUENCE: 42
atggaatgga gatggatctt tctcttcctc ctgtcaggaa ctacaggtgt ccactctgag      60
atccagctgc agcagtctgg acctgagctg gtgaagcctg ggcttcagt gaaggtatcc      120 tgcaaggctt ctggttatgc attcactagc tacaagatgt actgggtgaa gcagagccat     180
ggaaagagcc ttgagtggat tggatatatt gatccttaca atggtggtat taactacaac    240
cagatgttca agggcaaggc cacattgact gttgacaagt cctccagcac agcctacatg    300
catctcaaca gcctgacatc tgaggactct gcagtctatt actgtgcaag agccaaacaa    360
gacatgcccc ctccctggtt tgtttactgg ggccaaggga ctctggtcac tgtctctgca    420
```